(12) United States Patent
Nagashima

(10) Patent No.: US 8,773,272 B2
(45) Date of Patent: *Jul. 8, 2014

(54) LIGHT SCATTERING TYPE SMOKE DETECTOR

(75) Inventor: Tetsuya Nagashima, Tokyo (JP)

(73) Assignee: Hochiki Corporation, Tokyo (JP)

( * ) Notice: Subject to any disclaimer, the term of this patent is extended or adjusted under 35 U.S.C. 154(b) by 1030 days.

This patent is subject to a terminal disclaimer.

(21) Appl. No.: 12/683,926

(22) Filed: Jan. 7, 2010

(65) Prior Publication Data

US 2010/0118303 A1    May 13, 2010

Related U.S. Application Data

(63) Continuation of application No. 10/595,867, filed as application No. PCT/JP2004/017093 on Nov. 17, 2004, now Pat. No. 7,746,239.

(30) Foreign Application Priority Data

Nov. 17, 2003  (JP) .................................. 2003-386688
Nov. 17, 2003  (JP) .................................. 2003-386689

(51) Int. Cl.
*G08B 17/10*    (2006.01)

(52) U.S. Cl.
USPC ........... 340/630; 340/619; 340/628; 340/584; 250/216; 250/573; 250/574; 250/578.1; 356/438; 356/442; 356/448

(58) Field of Classification Search
USPC ............ 340/693.11, 628–634, 614, 615, 619, 340/584; 73/107.03, 107.05, 107.06, 73/107.07; 356/337–339, 438, 442, 448, 356/218, 222, 224, 229, 231, 234, 239.1, 356/239.2; 250/216, 573, 574, 578.1
See application file for complete search history.

(56) References Cited

U.S. PATENT DOCUMENTS

| | | | |
|---|---|---|---|
| 4,121,110 A * | 10/1978 | Solomon | ....................... 340/630 |
| 4,306,230 A | 12/1981 | Forss et al. | |
| 4,616,928 A | 10/1986 | Leavitt et al. | |
| 5,280,272 A | 1/1994 | Nagashima et al. | |
| 5,451,931 A | 9/1995 | Muller et al. | |
| 5,576,697 A | 11/1996 | Nagashima et al. | |
| 6,218,950 B1 | 4/2001 | Politze et al. | |
| 2002/0080040 A1 | 6/2002 | Schneider et al. | |

FOREIGN PATENT DOCUMENTS

| | | |
|---|---|---|
| EP | 0 877 345 | 11/1998 |
| GB | 2054922 A | 2/1981 |
| GB | 2 259 763 | 3/1993 |
| GB | 2 277 589 | 2/1994 |

(Continued)

OTHER PUBLICATIONS

European Patent Office, Extended European Search Report for corresponding European Pataent Application No. 04818558.1 dated Feb. 25, 2011.

*Primary Examiner* — Steven Lim
*Assistant Examiner* — Sisay Yacob
(74) *Attorney, Agent, or Firm* — Sherr & Jiang, PLLC

(57) ABSTRACT

A light scattering type smoke sensor includes a sensor body, light-emitter for emitting light toward an open smoke-sensing space and outputting a light-received signal according to the amount of scattering light received, and a fire judging unit for judging whether fire occurs or not on the basis of the amount of received light determined on the basis of the outputted light-received signal.

19 Claims, 36 Drawing Sheets

(56) References Cited

FOREIGN PATENT DOCUMENTS

| JP | 64-035694 | 2/1989 |
| JP | 01-251196 | 10/1989 |
| JP | 1251196 A | 10/1989 |
| JP | 04-260197 | 9/1992 |
| JP | 06-109631 | 4/1994 |
| JP | 10-188166 | 7/1998 |
| JP | 2000-222645 | 8/2000 |

* cited by examiner

F I G . 2 A
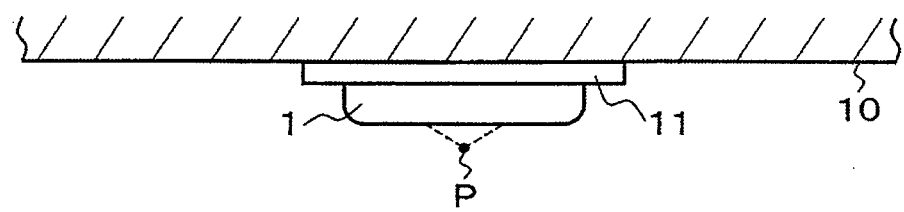
F I G . 2 B
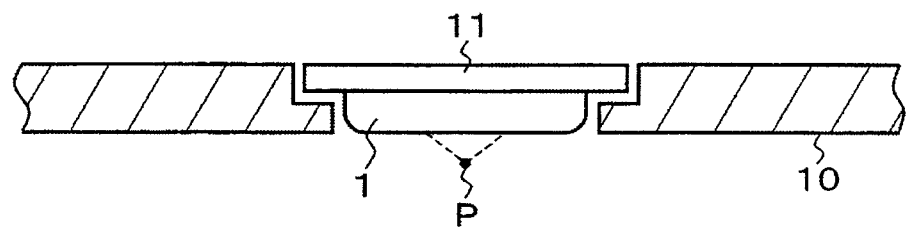

F I G. 5
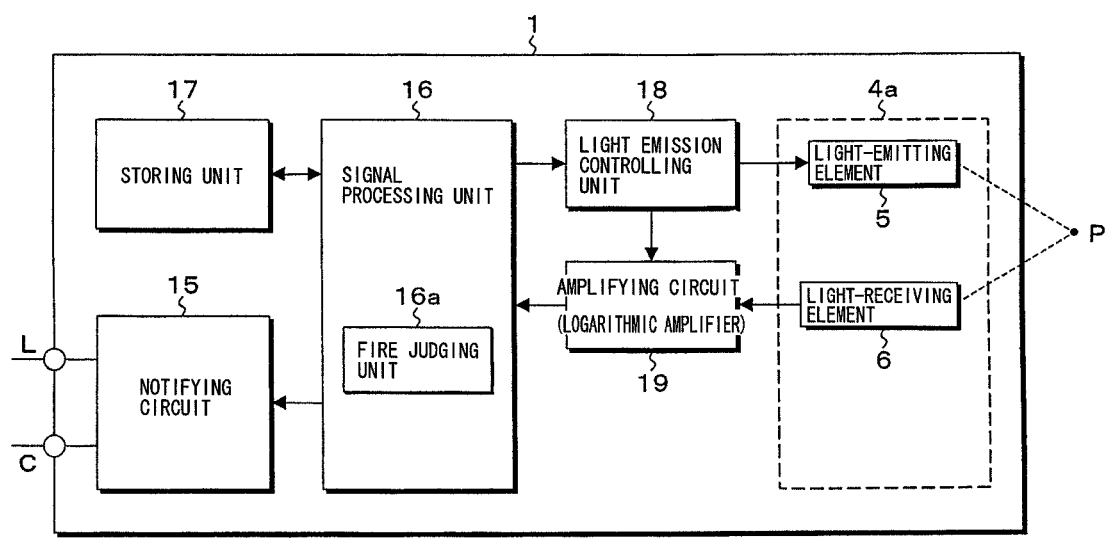

F I G. 7
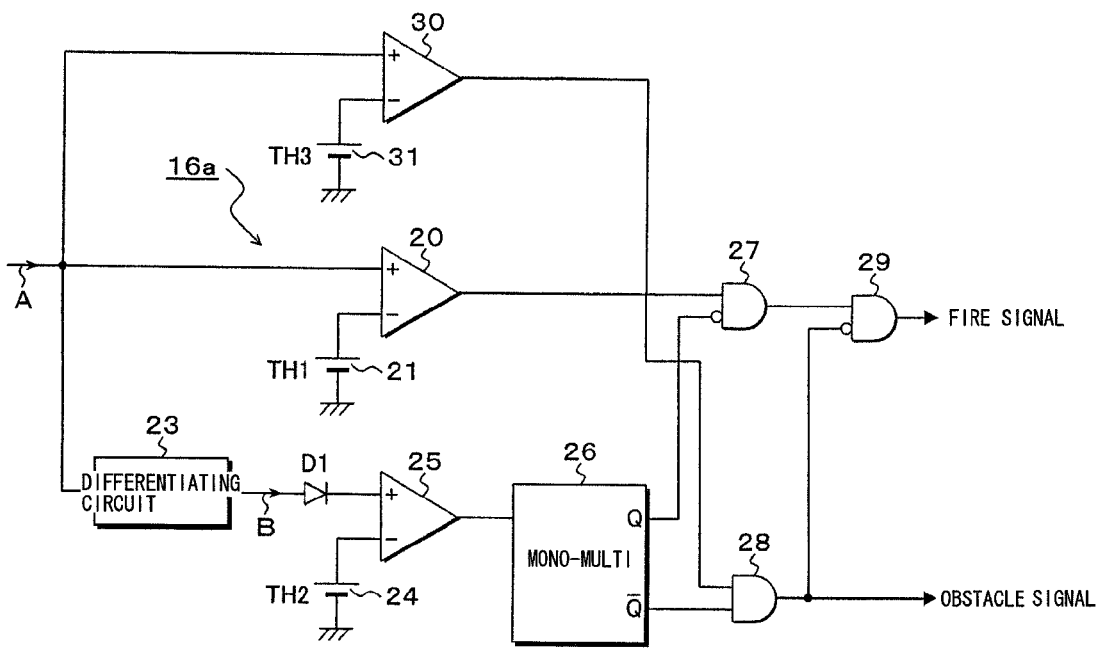

F I G . 1 2
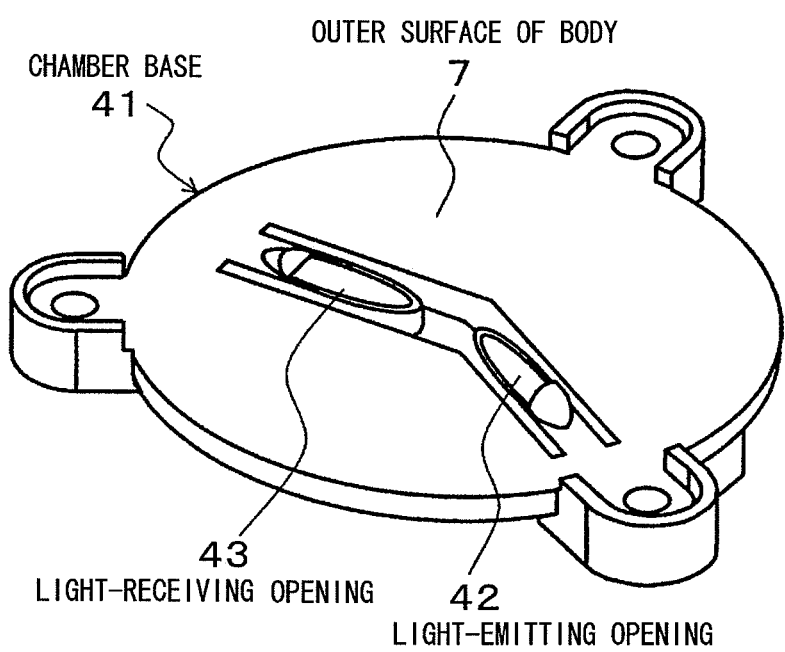

F I G . 1 3 A
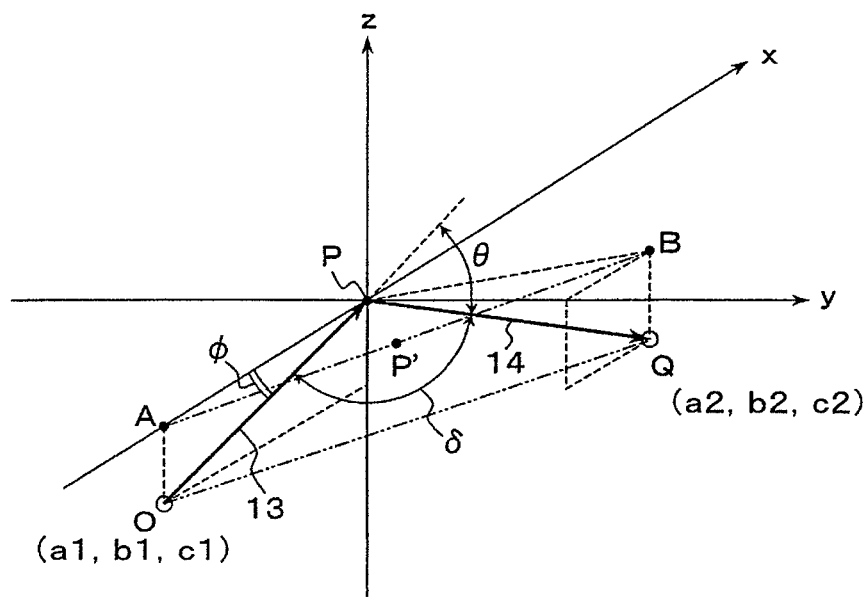
F I G . 1 3 B
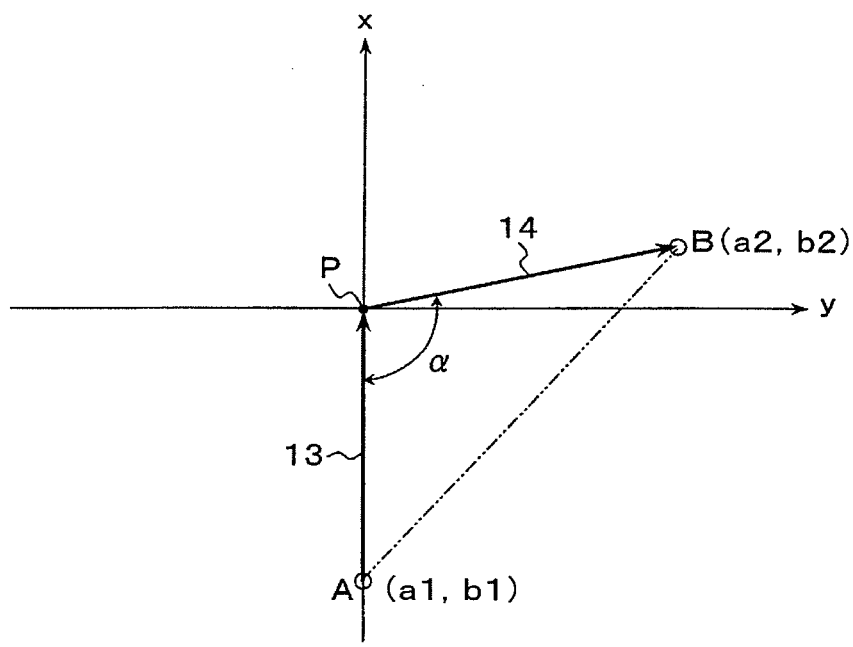

F I G. 18
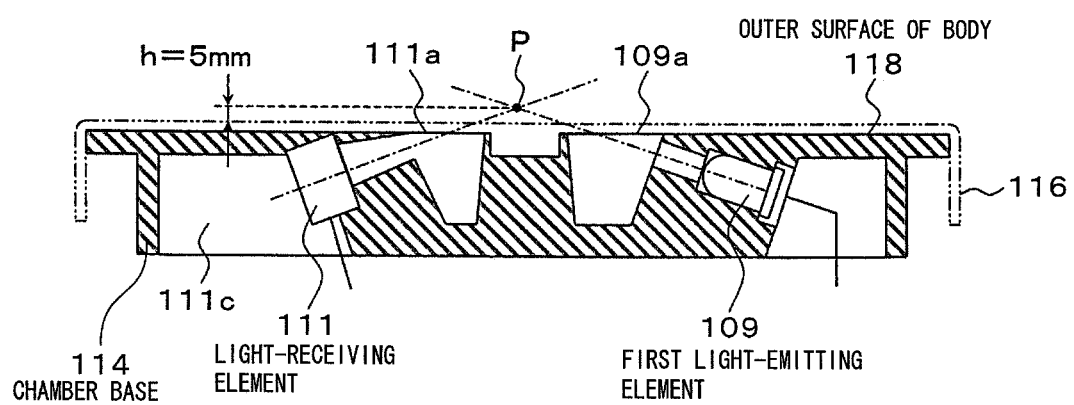

F I G . 2 0 A
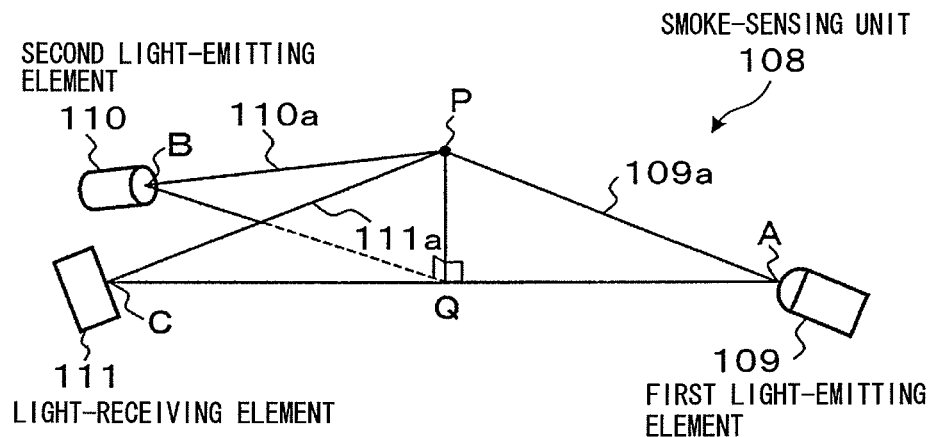
F I G . 2 0 B
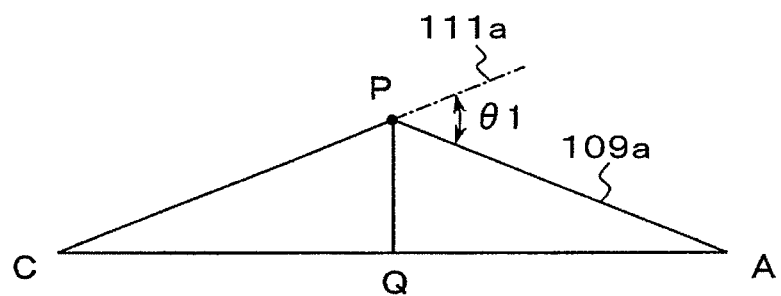
F I G . 2 0 C
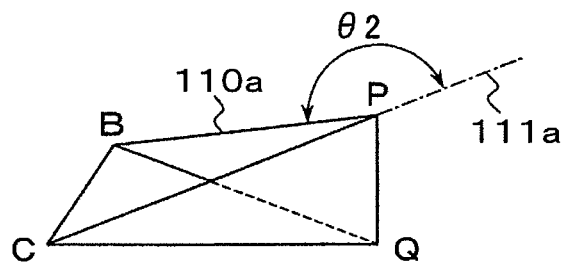

F I G. 25

| TYPE OF COMBUSTION MATERIAL | AMOUNT OF LIGHT-RECEIVED SIGNAL A1 FOR FIRST LIGHT-EMITTING ELEMENT | AMOUNT OF LIGHT-RECEIVED SIGNAL A2 FOR SECOND LIGHT EMITTING ELEMENT | RATIO $R = A1/A2$ |
|---|---|---|---|
| FUMIGATION SMOKE (COTTON LAMPWICK) | 6.0E−04 | 7.5E−05 | 8.0 |
| COMBUSTION SMOKE (KEROSENE) | 1.2E−04 | 5.3E−05 | 2.3 |

F I G. 2 6
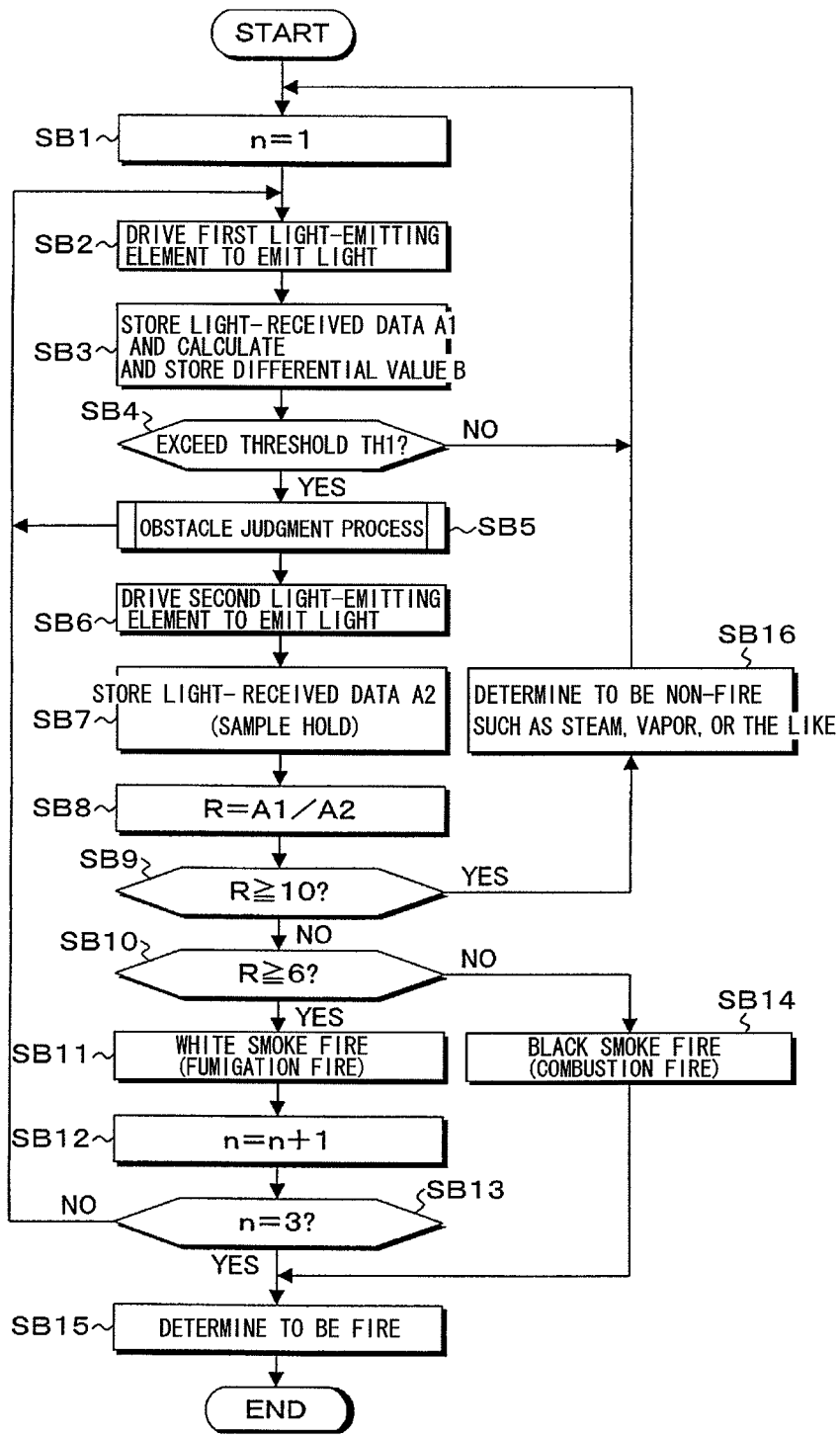

F I G. 30
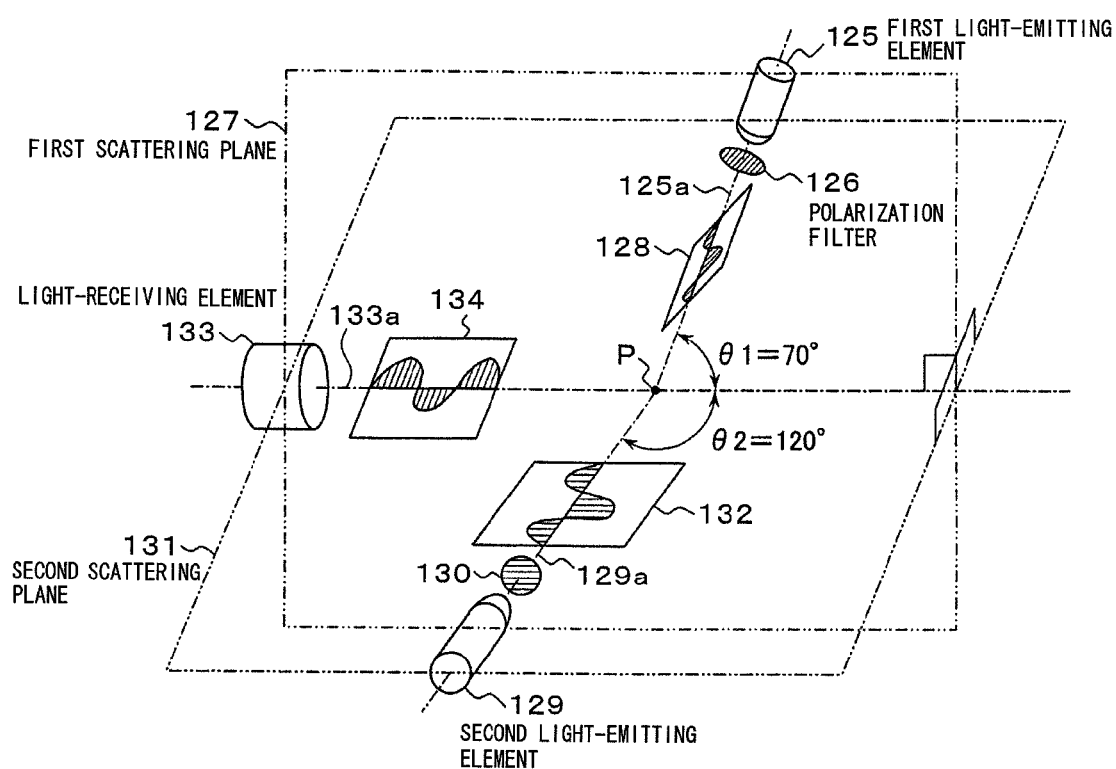

F I G. 31
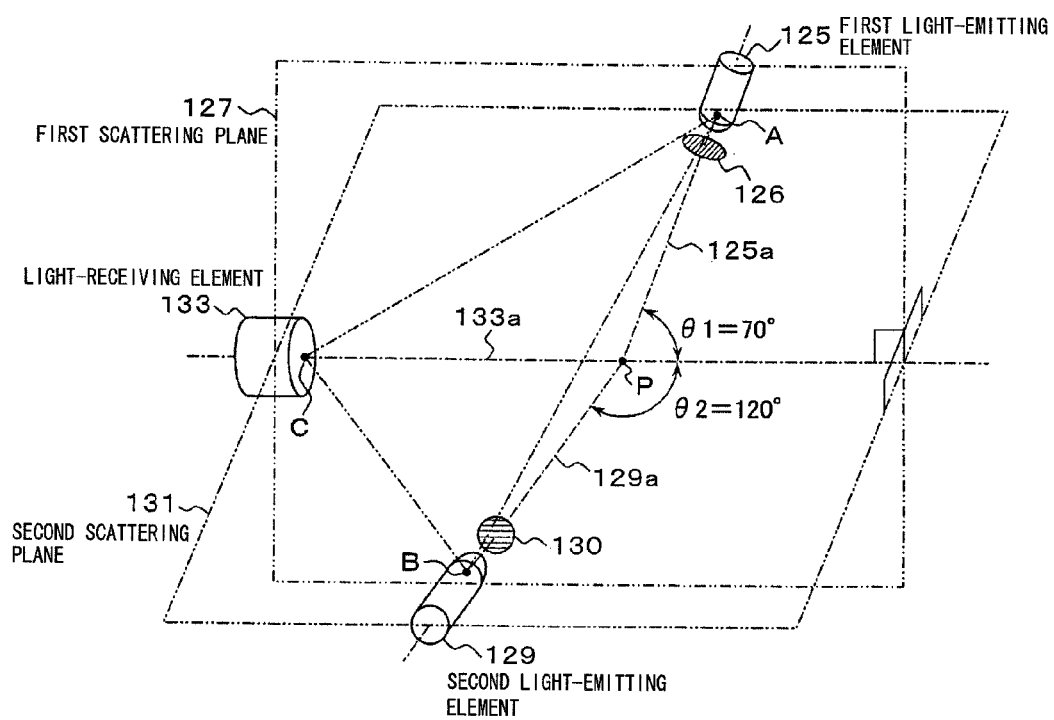

F I G. 3 2 A
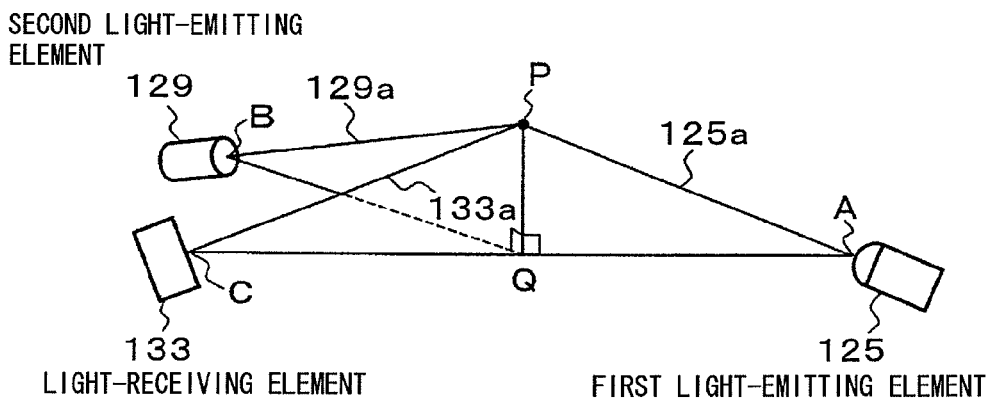
F I G. 3 2 B
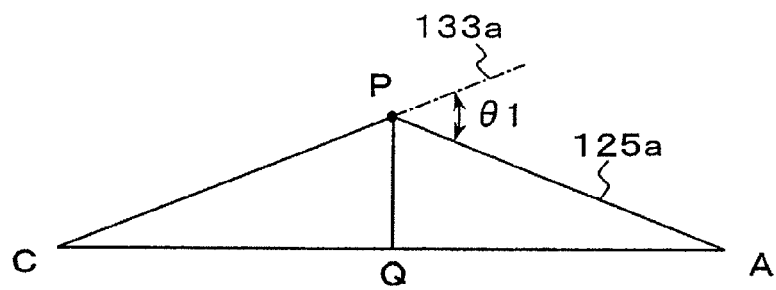
F I G. 3 2 C
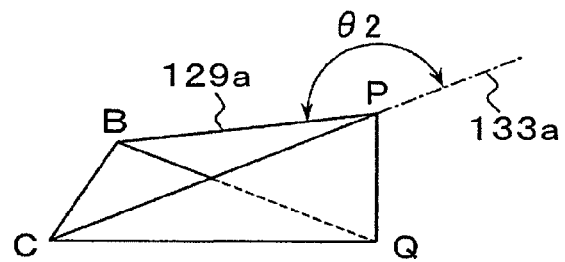

F I G. 33

| SCATTERING ANGLE | 70° | | 90° | | 120° | |
|---|---|---|---|---|---|---|
| POLARIZATION ANGLE φ | 0°(HORIZONTAL) | 90°(VERTICAL) | 0°(HORIZONTAL) | 90°(VERTICAL) | 0°(HORIZONTAL) | 90°(VERTICAL) |
| PAPER FILTER | 130 | 200 | 60 | 115 | 45 | 65 |
| KEROSENE | 20 | 56 | 18 | 47 | 10 | 40 |
| TOBACCO | 80 | 280 | 20 | 190 | 17 | 105 |

F I G. 34

| TYPE OF COMBUSTION MATERIALS | AMOUNT A1 OF LIGHT-RECEIVED SIGNAL FOR FIRST LIGHT-EMITTING ELEMENT | AMOUNT A2 OF LIGHT-RECEIVED SIGNAL FOR SECOND LIGHT-EMITTING ELEMENT | RATIO $R=A1/A2$ |
|---|---|---|---|
| PAPER FILTER | 200 | 45 | 4.44 |
| KEROSENE | 56 | 10 | 5.60 |
| TOBACCO | 280 | 17 | 16.47 |

F I G. 35
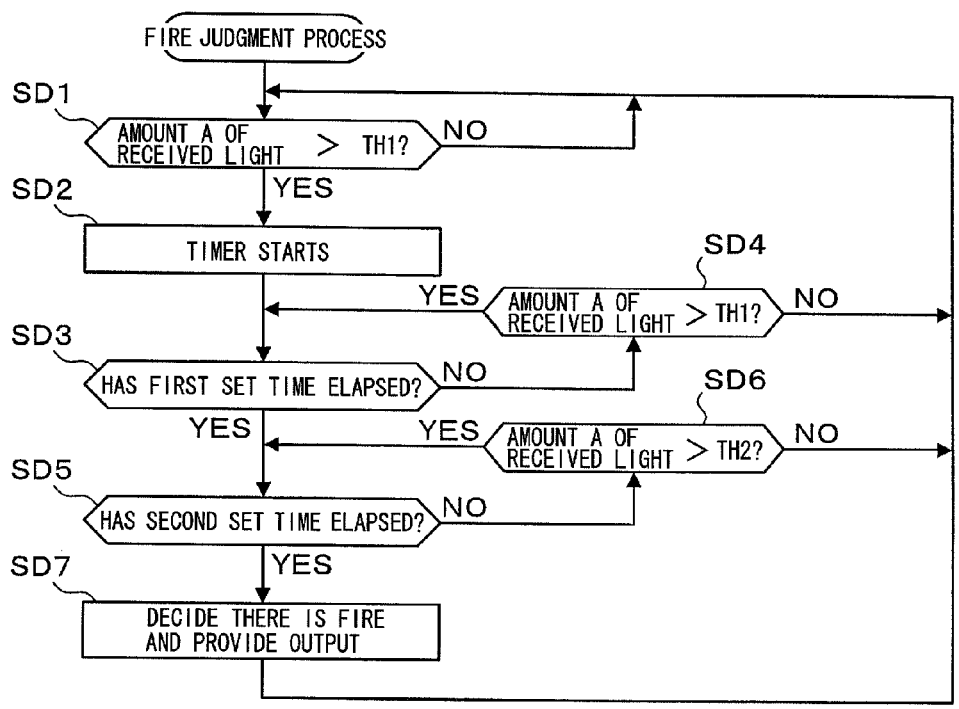

LIGHT SCATTERING TYPE SMOKE DETECTOR

CROSS REFERENCE TO PRIOR APPLICATIONS

This application is a Continuation of U.S. patent application Ser. No. 10/595,867 (filed on Mar. 28, 2007), which claims priority under 35 U.S.C. 119 and 35 U.S.C. 365 to Japanese Patent Application Nos. 2003-386688 and 2003-386689 (both filed on Nov. 17, 2003) and PCT Application No. PCT/JP2004/017093 (filed on Nov. 17, 2004), which are all hereby incorporated by reference in their entirety.

TECHNICAL FIELD

The present invention relates to a light scattering type smoke sensor which senses smoke by emitting light and detecting light scattered by the smoke.

BACKGROUND ART

A conventional light scattering type smoke sensor basically includes a smoke chamber through which smoke enters into the sensor from outside. An inside space of the smoke chamber functions as a smoke-sensing space, in which light emitted by a light-emitting element is scattered by smoke, and scattered light is received by a light-receiving element so that occurrence of fire can be detected.

The smoke-sensing space is provided inside the smoke chamber of the sensor in order to realize an accurate sensing of minute scattering light generated by reflection of light by the smoke without being affected by outside light, and also to prevent entrance of foreign substances into the smoke-sensing space. Presence of foreign substances such as a small insect in the smoke-sensing space may cause scattering of light and lead to false alarm. Therefore, the arrangement of the smoke-sensing space inside the smoke chamber is an essential part of the conventional light scattering type smoke sensor (see, for example, Patent Document 1 and Patent Document 2).

Patent Document 1: Japanese Patent Application Laid-Open No. H6-109631 Publication
Patent Document 2: Japanese Patent Application Laid-Open No. H7-12724 Publication

DISCLOSURE OF INVENTION

Problems to be Solved by the Invention

In the conventional light scattering type smoke sensor, however, the fact that the smoke chamber is a necessary structural element creates problems.

Firstly, in the conventional smoke sensor, a portion where the smoke chamber is arranged protrudes outwards so as to facilitate inflow of the smoke into the smoke chamber. When such a smoke sensor is arranged on a ceiling surface or the like, the portion sticks out from the ceiling surface which is visually undesirable when interior design is considered.

Further, since the smoke coming into the smoke chamber from outside passes through elements arranged around the smoke chamber, such as a cover, a smoke inlet, an insect screen, and a labyrinth for shielding outside light (light shielding wall), a desirable characteristic of smoke inflow cannot be obtained, and the sensing of smoke may delay.

Furthermore, when dusts or the like adhere or dew forms inside the smoke chamber while the smoke sensor is in an installed state, signal to noise ratio (S/N) may be deteriorated or false alarm may occur due to light reflected inside the smoke chamber. Hence, the smoke chamber needs to be cleaned and checked periodically, whereby maintenance cost increases.

If it is possible to eliminate the influence of outside light on the scattering light generated by smoke utilizing the characteristics of light wavelength or the polarization characteristics, the smoke chamber is not necessary for the formation of the smoke-sensing space inside the smoke sensor. Such solution is advantageous in various points, for example, in that it can eliminate inconveniences of the conventional smoke chamber.

In view of the above, an object of the present invention is to provide a smoke sensor which utilizes scattering light and which does not need a smoke chamber inside.

Mean(s) for Solving the Problems

In order to solve the problems as described above and to achieve an object, the present invention of claim 1 includes, a sensor body; a light-emitter that is incorporated in the sensor body to emit light toward an open smoke-sensing space located outside the sensor body; a light-receiver that is incorporated in the sensor body to receive scattered light generated by the light emitted from the light-emitter to the smoke-sensing space, and to output a light-received signal corresponding to an amount of received light scattered; and a fire judging unit that judges presence/absence of fire occurrence based on the amount of received light identified by the light-received signal output from the light-receiver.

The present invention of claim 2 according to claim 1, wherein the fire judging unit judges the present/absence of the fire occurrence based on the amount of received light and a differential value of the amount of received light.

The present invention of claim 3 according to claim 2, wherein the fire judging unit judges that fire occurs when the amount of received light exceeds a predetermined fire threshold and the differential value of the amount of received light is equal to or lower than a predetermined false alarm threshold.

The present invention of claim 4 according to claim 3, wherein when the amount of received light exceeds the predetermined fire threshold, and the differential value of the amount of received light exceeds the predetermined false alarm threshold, the fire judging unit checks whether the amount of received light exceeds a predetermined obstacle threshold or not when a predetermined time elapses since the time the differential value exceeds the predetermined false alarm threshold, and judges that there is an obstacle for fire sensing when the amount of received light exceeds the obstacle threshold.

The present invention of claim 5 according to claim 1, wherein the fire judging unit judges that fire occurs, when the amount of received light exceeds a predetermined first fire threshold for a time equal to or longer than a predetermined first set time, and the amount of received light exceeds a predetermined second fire threshold which is higher than the first fire threshold for a time equal to or longer than a predetermined second set time which is longer than the first set time.

The present invention of claim 6 according to any one of claims 1 to 5, wherein the light-emitter has plural light-emitters.

The present invention of claim 7 according to claim 6, wherein the light-emitter has first light-emitter that emits light of a first wavelength, and second light-emitter that emits light of a second wavelength which is shorter than the first wavelength, and a first scattering angle formed by mutual crossing of a light axis of the first light-emitter and a light axis of the light-receiving element is smaller than a second scattering angle formed by mutual crossing of a light axis of the second light-emitter and the light axis of the light-receiving element.

The present invention of claim 8 according to claim 7, wherein a central wavelength of the first wavelength is equal to or longer than 800 nm, a central wavelength of the second wavelength is equal to or shorter than 500 nm, the first scattering angle falls within a range of 20° to 50°, and the second scattering angle falls within a range of 100° to 150°.

The present invention of claim 9 according to claim 6, wherein the light-emitter has first light-emitter and second light-emitter, the first light-emitter emits light having a polarization plane vertical to a first scattering plane that passes through a light axis of the first light-emitter and a light axis of the light-receiving element, the second light-emitter emits light having a polarization plane parallel to a second scattering plane that passes through a light axis of the second light-emitter and the light axis of the light-receiving element, and a first scattering angle formed by mutual crossing of the light axis of the first light-emitter and the light axis of the light-receiving element is smaller than a second scattering angle formed by mutual crossing of the light axis of the second light-emitter and the light axis of the light-receiving element The present invention of claim 10 according to claim 9, wherein the first scattering angle is equal to or smaller than 80°, and the second scattering angle is equal to or larger than 100°.

The present invention of claim 11 according to any one of claims 6 to 10, wherein the plural light-emitters are arranged at solid angles, so that planes including respective light axes of the plural light-emitters and the light axis of the light-receiving element are substantially not identical with each other.

The present invention of claim 12 according to any one of claims 6 to 11, wherein the light-emitter includes first light-emitter and second light-emitter, the fire judging unit compares an amount of received light by the light-receiver with respect to scattered light generated from the light emitted by the first light-emitter and scattered by smoke, and an amount of received light by the light-receiver with respect to scattered light generated from the light emitted by the second light-emitter and scattered by the smoke, to identify a type of the smoke, and judges the presence/absence of fire occurrence based on a standard corresponding to the type of the smoke.

The present invention of claim 13 according to any one of claims 1 to 12, wherein a mutual crossing point of the light axis of the light-emitter and the light axis of the light-receiver in the smoke-sensing space is at least approximately 5 mm away from the sensor body.

The present invention of claim 14 according to any one of claims 1 to 13, wherein at least one portion of an outer surface of the sensor body is configured by an insect avoiding material, or an insect avoiding agent is applied or made to permeate to at least one portion of the outer surface of the sensor body.

The present invention of claim 15 according to any one of claims 1 to 14, wherein the light-receiver has an angle of field of view not larger than 5 degrees.

The present invention of claim 16 according to any one of claims 1 to 15, wherein the light-emitter emits collimated parallel beam.

The present invention of claim 17 according to any one of claims 1 to 16, further including a logarithmic amplifier which amplifies the light-received signal output from the light-receiver.

The present invention of claim 18 according to any one of claims 1 to 17, further including a light emission controller that drives the light-emitter to intermittently emit light by using a modulated light-emission signal, and an amplifier that amplifies the light-received signal output from the light-receiver in synchronization with the modulated light-emission signal.

The present invention of claim 19 according to claim 18, further including a light emission controller that drives the light-emitter to intermittently emit light by using a modulated light-emission signal, wherein the light-emitter emits light within a visible light wavelength band, and the light emission controller drives to intermittently emit light at a light-emission pulse width of equal to or smaller than 1 millisecond.

In embodiments, the light emission controller sets a total light emission time period in an intermittent light emission equal to or smaller than 1 millisecond.

Effect Of The Invention

According to the present invention, since light is emitted towards the smoke-sensing space outside the sensor body and received therefrom, the smoke-sensing point can be set outside the sensor body for smoke sensing. Therefore, the smoke chamber is not necessary, and the conventional structure in which the portion of the smoke chamber protrudes is not necessary, and the portion corresponding to the smoke chamber can be made flat and thin. As a result, when the light scattering type smoke sensor is installed on a ceiling surface, an outer surface of the sensor body which is located at a side of the smoke-sensing space can be made substantially coplanar to the ceiling surface, whereby a full-flat installation, i.e., an installation which does not make the sensor stick out from the ceiling surface, can be realized. Further, since the ceiling surface can be designed and constructed as a full-flat ceiling, the quality of interior design can be greatly improved. Still further, since the light scattered by the smoke is detected in the open space outside the outer surface of the sensor and the open outside space serves as the smoke-sensing space, there is no structural element that prevents the inflow of smoke dissimilar to the conventional smoke chamber. Hence, the smoke of the fire can be detected without delay. Still further, since the open outside space serves as the smoke-sensing space and the outer surface of the sensor body facing the open smoke-sensing space is exposed to the outside space below, no dust adhere to or dew forms on the surface. Therefore, the false alarm is not caused by such foreign substances, and no cleaning is required, whereby the maintenance cost can be reduced.

Further, according to the present invention, since fire judgment is performed based on the amount of received light and the differential value thereof, even when the insect or other foreign substances exist in the smoke-sensing space, false alarm can be prevented, whereby problems caused by the use of the open space as the smoke-sensing space can be eliminated.

Still further, according to the present invention, the smoke sensor decides that the fire occurs when the amount of received light exceeds the predetermined fire threshold, and the differential value of the amount of received light is not higher than the predetermined false alarm threshold. Since the increase in the smoke concentration caused by the fire proceeds moderately compared with the change in the amount of received light caused by foreign substances such as insects, the smoke sensor does not decide that the fire occurs even when the amount of received light reaches the level of the fire, and decides that the fire occurs only after the differential value thereof is confirmed to be equal to or less than the abnormal threshold. Thus, even when the foreign substances such as an insect exist in the smoke-sensing space, the false alarm of the smoke sensor can be prevented even more assuredly.

Still further, according to the present invention, when the amount of received light exceeds the predetermined obstacle threshold after the predetermined time elapses since the differential value exceeds the predetermined false alarm threshold, the smoke sensor decides that the foreign substance creates obstacle for sensing. The changes in the light-received signal caused by the foreign substances such as insect can be classified into a temporal change and a continuous change. Abnormal change in the light-received signal caused by incoming insects or the like is temporal and the light-received signal returns to a normal state after a certain time elapses since the differential value thereof exceeds the abnormal threshold value. Hence, if the light-received signal returns to a level equal to or lower than the obstacle threshold after a certain time, the cause of such changes can be decided as non-obstacle. On the other hand, when a spider's nest, curtain, or the like moves into or contacts with the smoke-sensing space, the light-received signal remains at the abnormal level over the obstacle threshold even after the certain time period elapses. In such case, the smoke sensor is in a troubled state where the smoke sensor cannot properly sense the smoke. When the smoke sensor is in such state, the smoke sensor regards such state as the obstacle and makes notification, whereby the maintenance check of the smoke sensor can be realized.

Still further, according to the present invention, when the amount of received light remains to be over the first fire threshold for a time period equal to or longer than the first set time, and when the amount of received light remains to be over the second fire threshold for a time period equal to or longer than the second set time, the smoke sensor decides that the fire occurs. In the conventional light scattering type smoke sensor and including the smoke chamber, it is difficult to distinguish the changes in smoke concentration of the smoke of the fire from the changes in smoke concentration of smoke cause by other reasons than fire (such as tobacco, or cooking), since the changes tend to be similar. Contrarily, the light scattering type smoke sensor of the present invention which does not need the smoke chamber has a characteristic that the different characteristics of the smoke of fire and the smoke caused by other reasons can be directly reflected in the sensing results. Thus, the smoke sensor of the present invention distinguishes two different types of smokes and prevents the false alarm.

Still further, according to the present invention, since the smoke sensor has plural light-emitters, the smoke sensor of the present invention can make multiple decision based on the plural data on the amounts of received light, whereby the decision on the occurrence of fire can be even more precisely made.

Still further, according to the present invention, two light-emitter emit light at different scattering angles to the light-receiving element. Hence, the light scattering characteristic of the smoke is made different for each type of the smoke. At the same time, two light-emitting units emit light of different wavelengths. Hence, the light scattering characteristic of the smoke is made different for each type of the smoke due to the light wavelengths. The combined effect of the differences in the light scattering angles and the light wavelengths creates a significant difference in scattering light intensity depending on the types of the smoke. Thus, the different types of smoke can be distinguished more accurately. Even though the smoke-sensing space is outside, the sensing of the smoke of fire can be accurately performed without being affected by the outside light. Further, alarm would not be raised by non-fire such as steam generated by cooking or smoke of tobacco. Still further, the smoke of fire can be distinguished based on the types of combusted materials, and the types of fire, such as black smoke fire and white smoke fire can be accurately distinguished.

Still further, according to the present invention, two light-emitting units have different polarization planes for each scattering plane of the light emitted therefrom. Hence, the light scattering characteristics can be made different according to the polarization directions of light. At the same time, since two light-emitting units have different scattering angles for the light-receiving element, light scattering characteristics can be made different depending on the types of smoke. The combined effect of the differences in the light polarization directions and the light scattering angles creates a significant difference in scattering light intensity depending on the types of smoke. Thus, the types of smoke can be distinguished more accurately. Even though the smoke-sensing space is in outside, the sensing of the smoke of fire can be accurately performed without being affected by the outside light. Further, alarm would not be raised by non-fire such as steam generated by cooking or smoke of tobacco. Still further, the smoke of fire such as black smoke fire and white smoke fire can be distinguished, and the types of combusted materials can be accurately distinguished.

Still further, according to the present invention, since the plural light-emitters are arranged at solid angles, the smoke-sensing point, which is a crossing point of the light axis of the light-emitter and the light axis of the light-receiver, can be arranged in a space outside the outer surface of the sensor body for the sensing of scattering light generated by the smoke.

Still further, according to the present invention, the amount of received scattering light generated by the light emitted from the first light-emitter is compared with the amount of received scattering light generated by the light emitted from the second light-emitter. For example, the ratio of the two is calculated and compared with the threshold. Based on the comparison, the type of the smoke is distinguished and the fire judgment is performed based on a different standard according to the type of smoke. Such multiple decision making based on the plural data of the amount of received light allows for still more accurate fire sensing.

Still further, according to the present invention, the crossing point of the light axis of the light-emitter and the light axis of the light-receiver is set at a point away from the sensor body by a distance equal to or longer than 5 mm. Hence, even when the dust adheres to the outer surface of the sensor body or an insect wriggles on the outer surface of the sensor body, such foreign substances do not affect the sensing.

Still further, according to the present invention, at least one portion of the outer surface of the sensor body is formed from an insect avoiding material or the like. Hence, the insects rarely approach the outer surface and the false alarm can be prevented in advance.

Still further, according to the present invention, the angle of field of view of the light-receiving unit is set equal to or narrower than 5 degrees. Thus, the size of the area for scattering light sensing can be set to a requisite minimum in the smoke-sensing space, and the influence of the outside light can be prevented.

Still further, according to the present invention, the light-emitter emits collimated parallel beam. Hence, the size of the area for the scattering light sensing can be set to a requisite minimum in the smoke-sensing space, and the influence of the outside light can be prevented.

Still further, according to the present invention, the light-received signal is amplified by a logarithmic amplifier. Hence, even when the outside light directly comes into the light-receiving element so that a normal linear amplifier undergoes output saturation so as to lose the function of amplification, the logarithmic amplifier does not undergo output saturation of received light so as to fail the amplification, whereby stable fire sensing can be allowed.

Still further, according to the present invention, the light-emitter is driven to intermittently emit light by a modulated light-emission signal, and the light-received signal is amplified in synchronization with the modulated light-emission signal. The modulated light emission and the synchronous light-received allow for the elimination of illumination light or the like which causes false alarm from a target of sensing, whereby the false alarm can be surely prevented from being caused by the outside light.

Still further, according to the present invention, since the light-emission pulse width is set equal to or smaller than 1 millisecond, the time period of light emission is not sufficient for the human visual sensitivity, whereby the human cannot recognize the blinking of the light-emitting unit of the smoke sensor.

Still further, according to the present invention, the total time period of light emission by the intermittent light emission driving is set to a length equal to or shorter than 1 millisecond. Hence, the light emission time period can be set so that the light is inperceptible for the human visual sensitivity, whereby the human cannot recognize the blinking of the light-emitting unit of the smoke sensor.

BRIEF DESCRIPTION OF DRAWINGS

FIG. 2A shows the light scattering type smoke sensor according to the first embodiment installed on a ceiling surface;

FIG. 2B shows the light scattering type smoke sensor according to the first embodiment embedded and installed in the ceiling surface;

FIG. 5 is a circuit block diagram of the light scattering type smoke sensor according to the first embodiment;

FIG. 7 is a circuit block diagram of a hardware in which a function of a fire judging unit in a signal processing unit of FIG. 5 is realized;

FIG. 12 is a perspective view of a chamber base of a light scattering type smoke sensor according to a second embodiment;

FIG. 13A is a schematic representation in three-dimensional coordinate space of an optical positional relation corresponding to positions of a light-emitting unit and a light-receiving unit in the chamber base of FIG. 12;

FIG. 13B is a diagram of a light axis of light emission and a light axis of light-received in a horizontal x-y plane;

FIG. 18 is a sectional view of an entire smoke-sensing unit including the chamber base of FIG. 17;

FIG. 20A shows a solid-angle arrangement of light axes of a first light-emitting element, a second light-emitting element, and a light-receiving element;

FIG. 20B shows the solid-angle arrangement of point A of the first light-emitting element and point C of the light-receiving element;

FIG. 20C shows the solid-angle arrangement of point B of the second light-emitting element and point C of the light-receiving element;

FIG. 25 shows amounts of light-received signals and ratio thereof for the fumigation smoke of the cotton lampwick and the combustion smoke of kerosene;

FIG. 26 is a flowchart of a fire sensing process performed in the circuit block of FIG. 19;

FIG. 30 is a schematic diagram of a configuration of a smoke-sensing unit according to a fourth embodiment;

FIG. 31 shows a solid-angle arrangement of the configuration of the smoke-sensing unit according to the fourth embodiment;

FIG. 32A shows a solid-angle arrangement of light axes of a first light-emitting element, a second light-emitting element, and a light-receiving element;

FIG. 32B shows the solid-angle arrangement of point A of the first light-emitting element and point C of the light-receiving element;

FIG. 32C shows the solid-angle arrangement of point B of the second light-emitting element and point C of the light-receiving element;

FIG. 33 shows experimental results of the amount of light-received signals for different types of smokes when the scattering angle and polarization angle are changed in the smoke-sensing unit having the configuration of FIG. 30;

FIG. 34 is a table of amount of light-received signal for different types of combusted materials and ratio thereof when the polarization direction and the scattering angle are set;

FIG. 35 is a flowchart of a fire judgment process according to a fifth embodiment;

Figure 1:
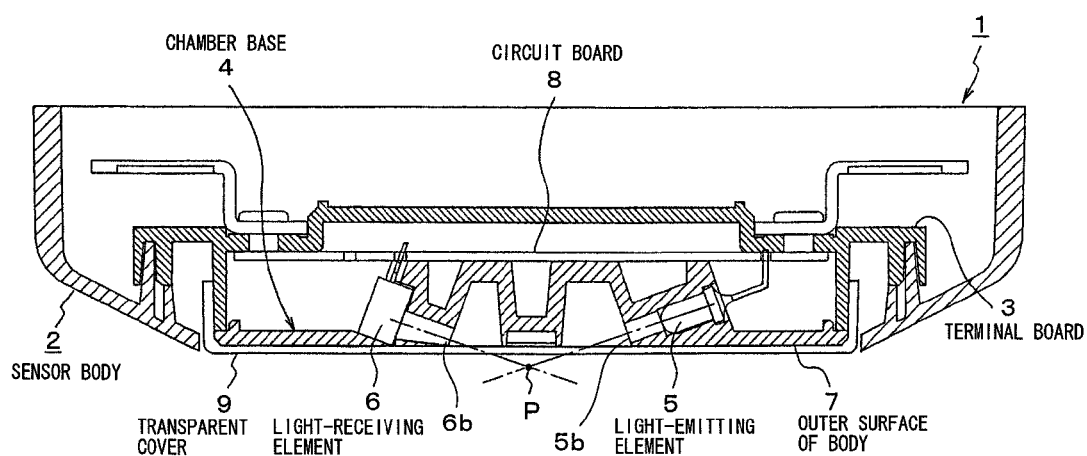
FIG. 1 is a sectional view of a light scattering type smoke sensor according to a first embodiment.

DESCRIPTION OF NOTATIONS 1, 40, 100 light scattering type smoke sensor
2, 112 sensor body
3, 113 terminal board
4, 41, 114 chamber base
4a, 108 smoke-sensing unit
5, 109, 110, 125, 129 light-emitting element (first light-emitting element, second light-emitting element)
5b, 42, 109b light-emitting opening
6, 111, 133 light-receiving element
6b, 43, 111b light-receiving opening
7 outer surface of sensor body
9, 116 transparent cover
11, 136 sensor base
15, 102 notifying circuit
16, 103 signal processing unit
17, 104 storing unit
18, 105, 106 light emission controlling unit (first light emission controlling unit, second light emission controlling unit)
19, 107 amplifying circuit
20, 25, 30 comparator
21, 24, 31 standard voltage source
23 differentiating circuit
26 monostable multivibrator
27, 28, 29 AND gate
126, 130 polarization filter

BEST MODE(S) FOR CARRYING OUT THE INVENTION

First, a light scattering type smoke sensor according to a first embodiment will be described. FIG. 1 is a sectional view of the light scattering type smoke sensor according to the first embodiment. In FIG. 1, a smoke sensor 1 using scattering light schematically includes a sensor body 2, a terminal board 3, a chamber base 4, a light-emitting element 5, a light-receiving element 6, and a transparent cover 9.

The terminal board 3 is housed inside the sensor body 2, and a circuit board 8 is housed inside the terminal board 3. The chamber base 4 is attached below the circuit board 8, and the chamber base 4 accommodates the light-emitting element 5 which serves as light-emitter, and the light-receiving element 6 which serves as light-receiver.

An outer surface 7 of the sensor body is a lower surface of the chamber base 4 and formed substantially flat, and the transparent cover 9 is attached to the outer surface 7 of the sensor body. Further, the outer surface 7 of the sensor body has a light-emitting opening 5b for ejecting the light emitted from the light-emitting element 5 to the outside of the smoke sensor 1 using scattering light, and a light-receiving opening 6b for introducing light thus ejected and scattered by smoke into the light-receiving element 6. In an outside open space further below the outer surface 7 of the sensor body, a light axis crossing point P is set, at which a light axis of the light-emitting element 5 and a light axis of the light-receiving element 6 mutually intersect with each other, and the light axis crossing point P constitutes a smoke-sensing point. Thus, one of characteristics of the smoke sensor 1 using scattering light according to the first embodiment is that the smoke-sensing point is set outside the smoke sensor 1 using the scattering light. Since the smoke-sensing space does not need to be formed inside the smoke sensor 1 using scattering light, a smoke chamber is not provided.

FIG. 2A shows a sensor base 11 which is a base for the attachment of the smoke sensor 1 using scattering light. In FIG. 2A, the sensor base 11 is installed onto a ceiling surface 10 and the smoke sensor 1 using scattering light of FIG. 1 is attached to the sensor base 11. As shown in FIG. 2A, since the smoke sensor 1 using scattering light does not include a smoke chamber which is embedded in the conventional light scattering type smoke sensor, the entire smoke sensor 1 using scattering light is thinner by the amount of the smoke chamber, and the smoke sensor 1 using scattering light does not protrude downward by a significant amount when the smoke sensor 1 is installed onto the ceiling surface 10 (in other words, the smoke sensor 1 using scattering light can be made relatively indistinctive against the ceiling surface 10).

FIG. 2B shows the sensor base 11 installed inside the ceiling surface 10 and the smoke sensor 1 using scattering light of FIG. 1 embedded and attached to the sensor base 11. As shown in FIG. 2B, a lower surface (the outer surface 7 of the sensor body and the transparent cover 9 of FIG. 1) of the smoke sensor 1 using scattering light can be arranged substantially coplanar with the ceiling surface 10. In this case, there is no protruding portion as the portion of the smoke chamber in the conventional smoke sensor. Hence a full-flat ceiling configuration can be realized. Particularly, since the smoke chamber is not necessary and the smoke sensor 1 using scattering light as a whole is made thinner, a portion embedded into the ceiling is smaller than in the conventional sensor, whereby the smoke sensor 1 using scattering light can be installed onto a narrow ceiling space.

Figure 3:
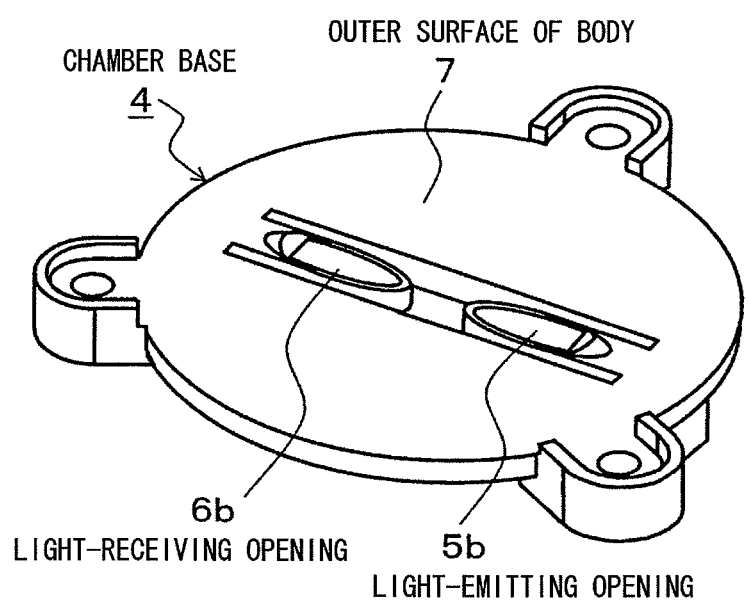
FIG. 3 is a perspective view of a chamber base.

FIG. 3 is a perspective view of the chamber base 4 in which the light-emitting element 5 and the light-receiving element 6 of FIG. 1 are arranged. In FIG. 3, the light-emitting opening 5b and the light-receiving opening 6b are formed on the outer surface 7 of the sensor body on a side of smoke sensing of the chamber base 4, and the light-emitting element 5 is embedded inside the light-emitting opening 5b, whereas the light-receiving element 6 is embedded inside the light-receiving opening 6b (light-emitting element 5 and light-receiving element 6 are not shown in FIG. 3).

Figure 4:
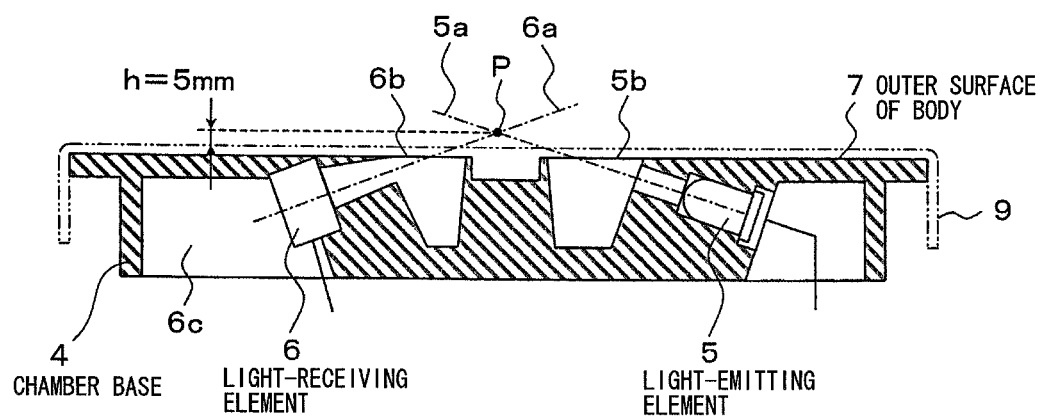
FIG. 4 is a sectional view of an entire smoke-sensing unit including the chamber base of FIG. 3.

FIG. 4 is a sectional view of an entire smoke-sensing unit including the chamber base 4 of FIG. 3 (here, the transparent cover 9 is shown by an imaginary line). In FIG. 4, an upper side of the chamber base 4 is formed as a flat outer surface 7 of the sensor body. In the outer surface 7 of the sensor body, the light emitting-opening 5*b* and the light-receiving opening 6*b* open and the transparent cover 9 is attached for protection. In the first embodiment, the outer surface 7 of the sensor body is made flat at the side of the smoke-sensing point P in the outside open smoke-sensing space, by way of example. The outer surface 7 of the sensor body, however, may be made slightly curved or may have some unevenness if necessary.

The light-emitting element 5 and the light-receiving element 6 are embedded inside the chamber base 4. A light axis 5*a* of light emission of the light-emitting element 5 intersects with a light axis 6*a* of light reception of the light-receiving element 6 at the smoke-sensing point P in the open smoke-sensing space outside the outer surface 7 of the sensor body. Here, height h from the outer surface 7 of the sensor body to the smoke-sensing point P which is the crossing point of light axes in the outside space can be set to any value, and preferably set to such a height that a factor of disturbance does not affect the smoke sensing. The factor of disturbance which may become obstacle for the smoke sensing outside the smoke sensor 1 using scattering light is, for example, dust or insect adhering to the outer surface 7 of the sensor body. For example, the height h can be set to a maximum height of an insect that gathers relatively frequently when the smoke sensor 1 using scattering light is installed. For example, it is preferable to secure at least 5 mm as height h.

The chamber base 4 may be configured of an insect-avoiding material to which insects rarely gather, or the insect-avoiding agent may be made to permeate or may be applied to the outer surface 7 of the sensor body. Here, the transparent cover 9 may be similarly configured by the insect-avoiding material, or the insect-avoiding agent may be made to permeate or may be applied to the transparent cover 9. Thus, the insects can be prevented from wriggling around on the outer surface of the transparent cover 9, whereby the false alarm can be prevented from being caused by the presence of insects. Any ingredients can be used as an ingredient of an actually applied insect-avoiding agent, and diethyl toluamide or pyrethroid may be applicable.

FIG. 5 is a circuit block diagram of the smoke sensor 1 using scattering light according to the first embodiment. In FIG. 5, the smoke sensor 1 using scattering light includes a smoke-sensing unit 4*a* having the light-emitting element 5 and the light-receiving element 6 as described above, a notifying circuit 15, a signal processing unit 16 employing a central processing unit (CPU), a storing unit 17, a light emission controlling unit 18, and an amplifying circuit 19.

In the above-described configuration, in brief, the light-emitting element 4*a* is driven by the light emission controlling unit 18 to emit light. Thus emitted light is reflected by smoke at the smoke-sensing point P outside the smoke sensor 1 using scattering light and surroundings thereof, and scattered. The scattered light is received by the light-receiving element 6. The output of the light-receiving element 6 is amplified by the amplifying circuit (logarithmic amplifier) 19, and supplied as an input to the signal processing unit 16. The signal processing unit 16 compares the output level of the light-receiving element 6 supplied as an output from the amplifying circuit 19 with a fire threshold TH1, a false alarm threshold TH2, or an obstacle threshold TH3; the fire threshold TH1, the false alarm threshold TH2, and the obstacle threshold TH3 are stored in the storing unit 17 in advance, as described later, to decide whether the fire occurs or not, whether it is a false alarm or not, or whether there is an obstacle or not. When a predetermined condition is satisfied, the signal processing unit 16 operates the notifying circuit 15 to send out a fire signal to a predetermined receiver.

The signal processing unit 16 has a function of a fire judging unit 16*a* as a function under programmed control. The fire judging unit 16*a* performs fire judgment, in other words, the fire judging unit 16*a* decides whether the fire occurs or not based on the light-received signal from the light-receiving element 6 and a differential value thereof. Specifically, the fire judging unit 16*a* decides that the fire occurs when the light-received signal A from the light-receiving element 6 exceeds the predetermined fire threshold TH1, and a differential value B of the light-received signal A does not exceed the predetermined false alarm threshold TH2.

On the other hand, when light-received signal A of the light-receiving element 6 exceeds the predetermined fire threshold TH1, and the differential value of the light-received signal B exceeds the predetermined false alarm threshold TH2, the fire judging unit 16*a* decides whether the light-received signal A exceeds the predetermined obstacle threshold TH3 or not when a predetermined time period T elapses since the differential value B exceeds the predetermined false alarm threshold TH2. When the light-received signal A is lower than the obstacle threshold TH3, the fire judging unit 16*a* decides that the obstacle is temporal and continues monitoring. On the other hand, when the light-received signal A exceeds the obstacle threshold TH3, the fire judging unit 16*a* decides that the obstacle is caused by foreign substance.

Figure 6:
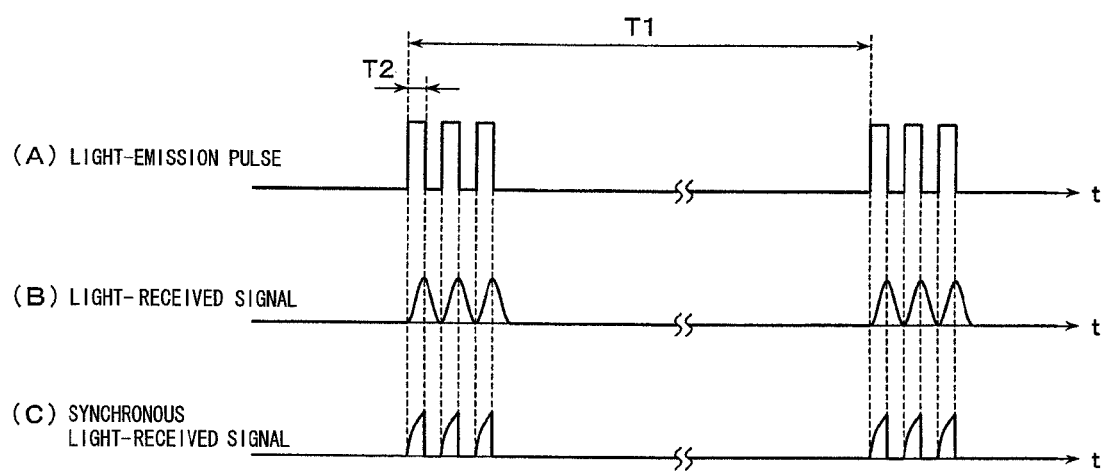
FIG. 6 is a time chart of driving for light emission by a light emission controlling unit of FIG. 5.

FIG. 6 is a time chart of light emission driving by the light emission controlling unit 18 of FIG. 5. In FIG. 6, light-emission pulse (A) indicates the light emitted from the light-emitting element 5 of FIG. 1, the light-received signal (B) indicates the light received by the light-receiving element 6 of FIG. 1, and synchronous light-received signal (C) indicates an amplified version of a light-received signal acquired by amplification in the amplifying circuit 19 of FIG. 5. Here, the light emission controlling unit 18 drives the light-emitting element 5 so that the light-emitting element 5 emits light as light-emission pulse (A) having pulse width T2 and being cyclically output every cycle T1. The light emission controlling unit 18 thus makes the light-emitting element 5 perform modulated light emission. Accordingly, the amplifying circuit 19 synchronizes with the modulation of the light emission controlling unit 18, and acquires the synchronous light-received signal (C) which is the light-received signal (B) in synchronization with the light emission modulation.

Here, the cycle T1 of light emission is, for example, T1=1 second, and the pulse width T2 of the modulated light emission is, for example, T2=50 microseconds. Thus, the modulated light emission and the corresponding synchronous light reception allow for elimination of light-received signal generated by incidence of light other than the light scattered by the smoke in the outside smoke-sensing space, and only the scattered light by the smoke is surely received.

Further, since the light emission wavelength band of the light-emitting element 5 is within the visible light band, the light emission time period is restricted to a time period equal to or less than 1 millisecond so that the human cannot recognize the intermittently emitted light. For the human to visually recognize the light from the light-emitting element, the light must be emitted continuously over more than 1 millisecond. Here, the light emission time period is restricted to a time period equal to or less than 1 millisecond, so that the human cannot see the light from the light-emitting element.

In the case of light-emission pulse (A) of FIG. 6, it is sufficient to set the total light emission time period of three light-emission pulses (pulse width T2×3) to a time period equal to or less than 1 millisecond. For example, if T2=50 microseconds as described above, the total light emission time period of three light-emission pulses is 150 microseconds, which is less than 1 millisecond. Hence the emitted light cannot be seen.

FIG. 7 is a circuit block diagram in which the processing function of the fire judging unit 16a in the signal processing unit 16 of FIG. 5 is realized by hardware. In FIG. 7, the fire judging unit 16a configured by hardware includes a comparator 20, a standard voltage source 21, a differentiating circuit 23, a comparator 25, a standard voltage source 24, a comparator 30, a standard voltage source 31, a monostable multivibrator 26, AND gates 27, 28, 29, and the like connected with each other as shown.

The comparator 20 receives as an input the amplified light-received signal A which is obtained through amplification of the light-received output from the light-emitting element 6 at the amplifying circuit 19, compares the amplified light-received signal A with the predetermined fire threshold TH1 set by the standard voltage source 21, and outputs a signal of H level (High output) when the level of the amplified received signal A exceeds the fire threshold TH1. The H level output of the comparator 20 is supplied to one input of the AND gate 27.

The comparator 30 receives as an input the amplified light-received signal A which is obtained by amplification of the received light output of the light-receiving element 6 at the amplifying circuit 19, compares the amplified light-received signal A with the obstacle threshold TH3 set by the standard voltage source 31, and outputs a signal of H level when the level of the amplified light-received signal A exceeds the obstacle threshold TH3. The H level output of the comparator 30 is supplied to one input of the AND gate 28.

The light-received signal A is differentiated by the differentiating circuit 23. The differentiated signal is supplied to the comparator 25 via diode D1 as the differential value B. The comparator 25 compares the predetermined abnormal threshold TH2 set by the standard voltage source 24 and the differential value B. When the differential value B exceeds the abnormal threshold TH2, the comparator 25 supplies a signal of H level as an output. Here, the diode D1 obtains differentiated signal with both positive polarity and negative polarity from the differentiating circuit 23, and takes out only the differential value of positive polarity.

The H level output from the comparator 25 is supplied to the monostable multivibrator 26. The monostable multivibrator 26 is driven when receiving the H level output, and supplies H level output from output Q over a predetermined time period T. The signal supplied from the output Q of the monostable multivibrator 26 is inverted and supplied to another input of the AND gate 27.

Hence, when the differential value B exceeds the abnormal threshold TH2 at the comparator 25, and the monostable multivibrator 26 supplies H level output for time period T1, the AND gate 27 prohibits an output of a fire-sensing signal of H level supplied from the comparator 20. Further, when the differential value B does not exceed the abnormal threshold TH2 at the comparator 25, the signal from the output Q of the monostable multivibrator 26 is at L level (Low level). Hence, the AND gate 27 is in a permission state so as to output the H level output supplied from the comparator 20 as it is to indicate fire sensing.

The output of the AND gate 27 is supplied to one input of the AND gate 29. The output of the AND gate 28 is inverted and supplied to another input of the AND gate 29. The AND gate 28 receives the output from the comparator 30 and the inverted output from the monostable multivibrator 26. Hence, the AND gate 28 turns into the permission state in response to the inverted output provided when the monostable multivibrator 26, after operating for T time period according to the H level output from the comparator 25, is turned off, while the comparator 30 successively supplies the H level output by detecting the obstacle. Then, the output of the comparator 30 is supplied as an output from the AND gate 28, which serves as an obstacle signal.

Further, when the AND gate 28 supplies the obstacle signal which is the H level output, the AND gate 29 is in a prohibited state due to the inverted input thereof. The H level output from the comparator 30 is prohibited by the AND gate 29, and when the obstacle signal is output, the output of the fire signal is prohibited.

Figure 8:
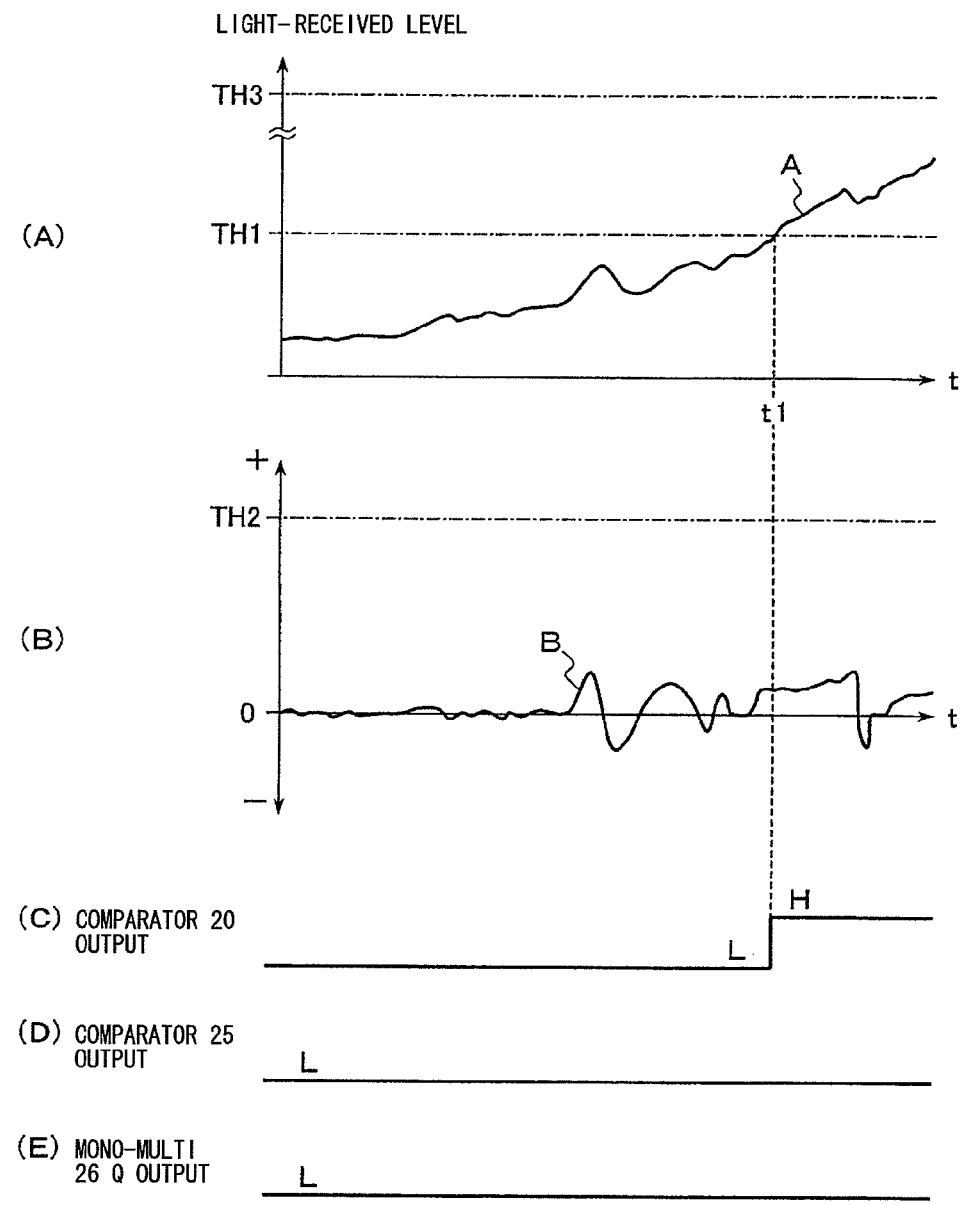
FIG. 8 is a time chart of an operation of the fire judging unit of FIG. 7 when the smoke sensor receives smoke of fire.

FIG. 8 is a time chart of an operation of the fire judging unit 16a of FIG. 7 when the smoke sensor receives smoke of fire.

When the smoke sensor received the smoke of fire, the light-received signal A of the light-receiving element 6 gradually increases over the time as shown in section (A) of FIG. 8. When the light-received signal A exceeds the fire threshold TH1 at time t1, the output of the comparator 20 attains H level. Then, since the AND gates 27 and 29 are in permission state, the fire signal attains H level as shown in section (C) of FIG. 8, and the notifying circuit 15 of FIG. 5 operates to send out the fire signal to the receiver side.

Here, the differential value B of the light-received signal A of the differentiating circuit 23 is relatively small and does not exceed the abnormal threshold TH2 since the increase in smoke concentration is relatively mild.

Figure 9:
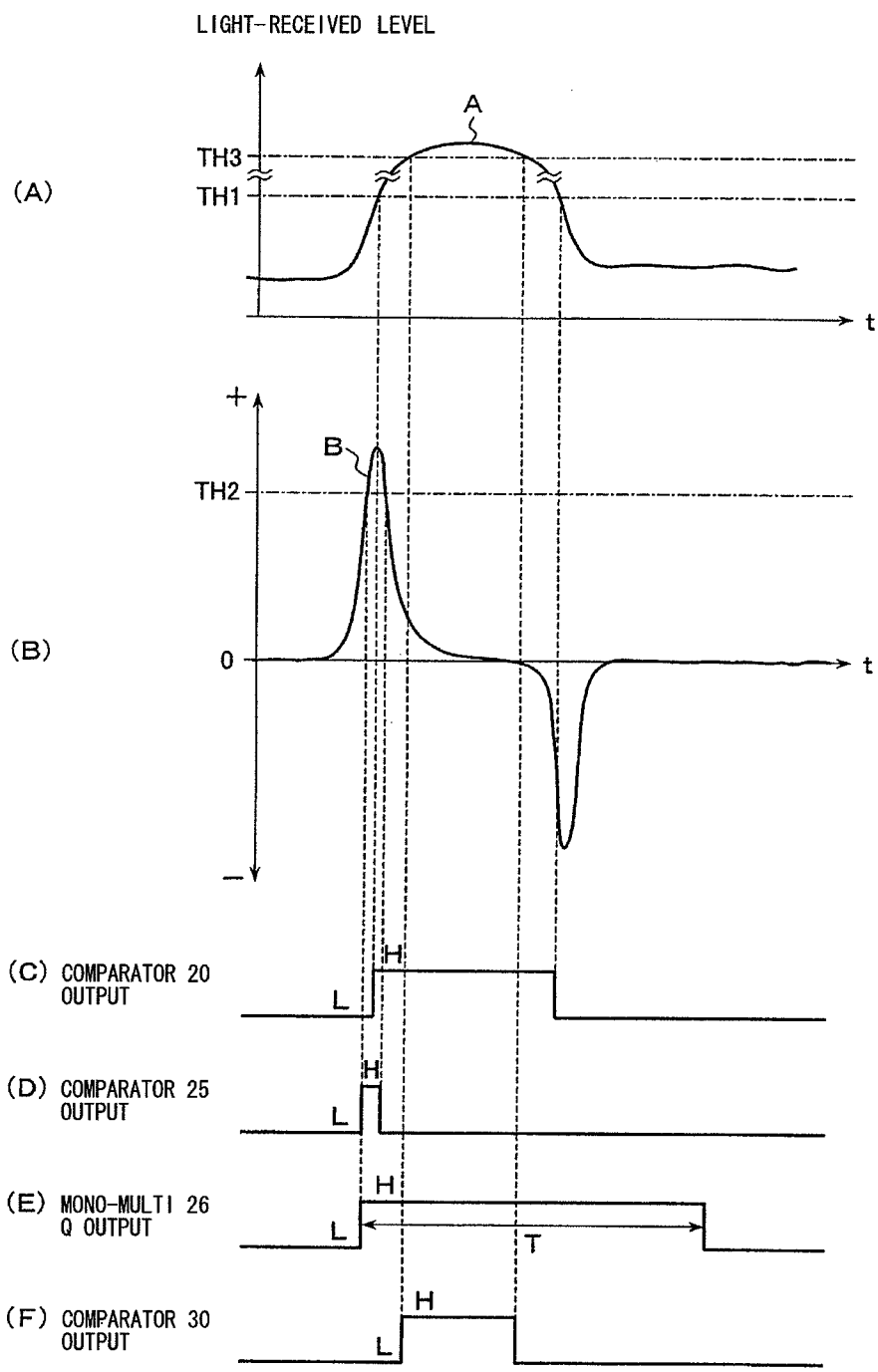
FIG. 9 is a time chart of a temporal increase in scattering light.

FIG. 9 is a time chart obtained when the scattered light temporarily increases due to flying insect passes over the smoke-sensing point P in the outside open space below the outer surface 7 of the sensor body in the smoke sensor 1 using scattering light of FIG. 1. When the scattered light is temporarily generated, the light-received signal A suddenly increases and then returns to a normal level as shown in section (A) of FIG. 9. While the light-received signal A is above the fire threshold TH1, the output of the comparator 20 attains H level as shown in section (C) of FIG. 9.

On the other hand, the differential value B of the light-received signal A at the differentiating circuit 23 rises by a significant degree to a positive direction at the rising of the light-received signal A, and is lowered significantly to a negative direction at the falling of the light-received signal B as shown in section (B) of FIG. 9. When the differential value B significantly changes to the positive direction, the level thereof exceeds the abnormal threshold TH2, and the comparator 25 supplies an H level output as shown in section (D) of FIG. 9. As a result, the output from the output Q of the monostable multivibrator attains H level as shown in section (E) of FIG. 9.

Hence, even when the output of the comparator 20 attains H level, a signal from the output Q of the monostable multivibrator 26 attains H level, thereby prohibiting the output of the fire signal from the AND gate 27. As a result, even when the insect or the like temporarily passes over the smoke-sensing point P in the outside open space, the false alarm, i.e., the output of the fire signal does not happen.

The set time T of the monostable multivibrator 26 may be set so that the time required for the foreign substance to pass through the smoke-sensing point is sufficiently covered. The foreign substance passes over the smoke-sensing point outside, for example, when the person's finger or a matter other than the insect passes over the smoke-sensing point.

Figure 10:
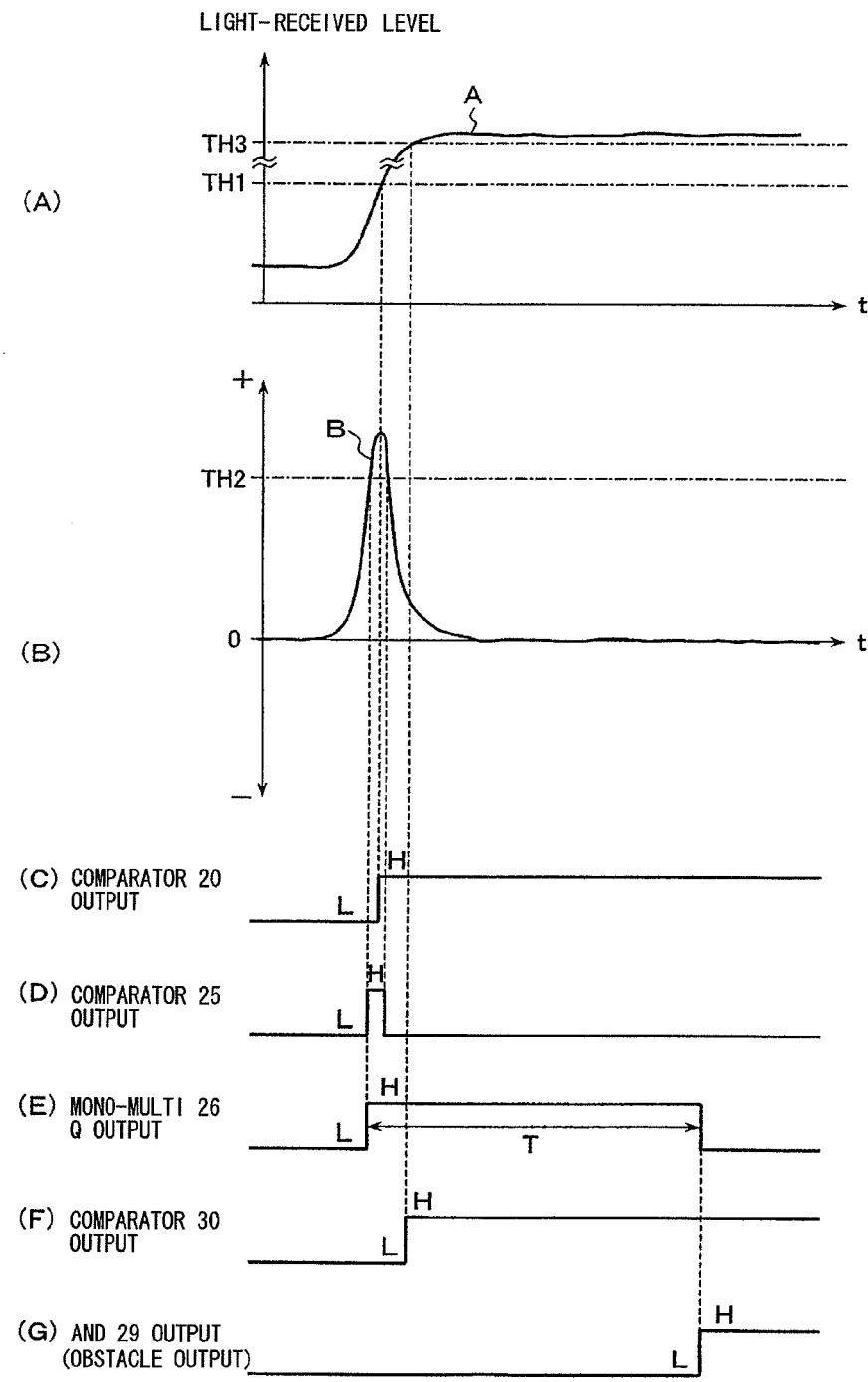
FIG. 10 is a time chart obtained when a foreign substance adheres to an outer surface of a sensor body near smoke-sensing point P.

FIG. 10 is a time chart obtained when the foreign substance such as a curtain adheres to the outer surface 7 of the sensor body near the smoke-sensing point P set in the outside space of FIG. 1. When the foreign substance fixedly adheres, the light-received signal rises by a significant degree over the fire threshold TH1 as shown in section (A) of FIG. 10 and exceeds and maintains a level over the obstacle threshold TH3.

The differential value B output from the differentiating circuit 23 changes by a significant degree to a positive direction as shown in section (B) of FIG. 10, and temporarily exceeds the abnormal threshold TH2. Hence, the comparator 25 for the abnormal sensing also supplies H level output according to the temporal increase in the differential value, to operate the monostable multivibrator 26, and then the monostable multivibrator 26 supplies H level output for a predetermined time period T as shown in section (E) of FIG. 10.

Then due to the signal supplied from the output Q of the monostable multivibrator 26, the AND gate 27 attains prohibited state, and does not supply H level output while the monostable multivibrator 26 operates. When the monostable multivibrator 26 is turned off after a predetermined time period to supply L level output from the output Q, the prohibition of the AND gate is canceled, and H level output is supplied. At the same time, the AND gate 28 attains permission state at the rising of the inverted output of the monostable multivibrator 26 to the H level. Then, the AND gate 28 supplies the H level output on receiving the H level output from the comparator 30 since the level of the light-received signal A is over the obstacle threshold TH3. Then, the H level output of the AND gate 28 is supplied as the obstacle signal (trouble signal) as an output.

Simultaneously, the H level output of the AND gate 28 turns the AND gate 29 into prohibited state, and even when the H level output is provided from the AND gate 27, the output thereof is prohibited and not supplied as the fire signal.

The obstacle signal generated by the H level output of the AND gate 28 is supplied to the notifying circuit 15 of FIG. 5. When the obstacle signal is sent in a different signal form from the signal sent as the fire alarm to the receiver, the receiver side can give an obstacle-indicating display to notify the trouble of the sensor. Then, personnel can check the outer surface 7 of the sensor body on the side of smoke sensing and remove the adhered foreign substance or the like to eliminate the trouble. The notifying circuit 15 may realize the transmission of the obstacle signal to the receiver by making a notifying electric current flow as pulses for a predetermined time period, for example.

Figure 11:
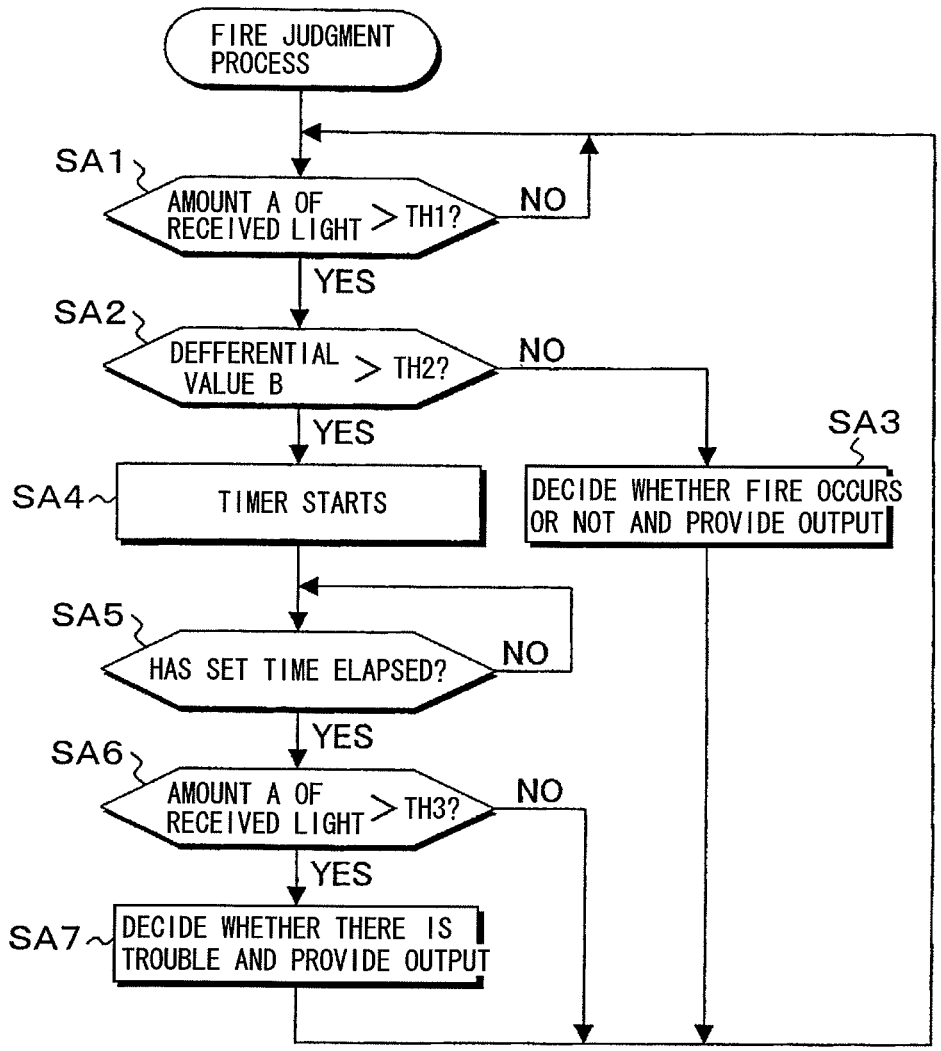
FIG. 11 is a flowchart of a process for executing the function of the fire judging unit in the signal processing unit of FIG. 5 through programmed control.

Here, the output control of the fire signal or the obstacle signal may be realized by software logic other than the wired logic shown in FIG. 7. FIG. 11 shows a flowchart of programmed controlled processing of the fire judging unit 16a in the signal processing unit 16 of FIG. 5. By a program different from that executes the fire judgment process of FIG. 11, sampling of the light-received signal A supplied from the amplifying circuit 19 and the computation of the differential value through the differentiating process of the sampled light-received signal value are repeatedly performed.

In the fire judgment process of FIG. 11, it is checked whether the received light value A is below the predetermined fire threshold TH1 or not in step SA1. When the received light value A exceeds the fire threshold TH1, the process proceeds to step SA2, to check whether the differential value B is below the predetermined abnormal threshold TH2 or not. When the differential value B is below the abnormal threshold TH2, the process proceeds to step SA3, and it is decided that the fire occurs and the output is supplied to indicate that there is a fire.

When the differential value B exceeds the abnormal threshold TH2 in step SA2, the process proceeds to step SA4, and the timer set to the set time T starts counting. After the timer starts, the elapse of the set time T is checked in step SA5. When the set time elapses, the process proceeds to step SA6 to check whether the received light value A exceeds the obstacle threshold TH3 or not.

When the received light value A is not above the obstacle threshold TH3, similarly to the case shown in FIG. 9, it means that the increase in received light is caused merely by a temporal increase of scattered light, and no particular output is supplied regarding fire occurrence. On the other hand, when the received light value A exceeds the obstacle threshold TH3, the abnormal light-received signal is successively obtained as shown in FIG. 10. Then, it is determined that the obstacle exists in step SA7, and the output is supplied to indicate the presence of the obstacle.

In the first embodiment, as shown in FIG. 5, the received light output from the light-receiving element 6 is amplified by the amplifying circuit 19 which is a logarithmic amplifier, whereby it can be decided whether the fire occurs or not even more accurately. When the received light output is amplified by a normal linear amplifier, the amplifier output may become saturated under the environment with a strong disturbing light, and false fire alarms may be raised. In the first embodiment, since the received light output is amplified by a logarithmic amplifier, even when a relatively strong disturbing light comes into the light-receiving unit, the amplifier output would not become saturated and the sensor does not become incapable of detecting the scattered light by the smoke. In addition, when the scattered light by the smoke is detected by the logarithmic amplifier under the environment with disturbing light, the range of variation in the amplifier output corresponding to the smoke becomes small. Since the smoke sensor of the first embodiment calculates the differential value, signal to noise (S/N) ratio is improved and it can be decided whether the fire occurs or not.

Thus, according to the first embodiment, since the smoke chamber is eliminated, the light scattering type smoke sensor can be configured into a flat shape with little protrusions, and a full-flat installation, i.e., an installation without protrusions from the ceiling surface can be realized.

Further, since it is decided whether the fire occurs or not based on the received light amount and the differential value thereof, even when the foreign substances such as insects are present in the smoke-sensing space, false alarm of the smoke sensor can be prevented, and the problem caused by the use of an open space as the smoke-sensing space can be eliminated.

Further, since the sensor does not decide immediately that fire occurs even when the received light amount reaches the fire level, and decides that fire occurs based on a condition that the differential value of the received light amount is not higher than the abnormal threshold, false alarm which may be caused by the presence of foreign substances such as insects in the smoke-sensing space can be even more surely prevented.

Further, when the differential value remains at the level above the abnormal threshold even after the elapse of a predetermined time period, the sensor decides that there is an obstacle and gives a notification, whereby the maintenance and check of the smoke sensor can be realized.

Further, since the smoke-sensing point is set away from the sensor body by at least 5 mm, even when the dust adheres to the outer surface of the sensor body or the insect wriggles on the outer surface of the sensor body, such foreign substances do not affect the fire sensing.

Further, since at least a portion of the outer surface of the sensor body is configured by the insect-avoiding material or the like, the insects rarely approaches the outer surface and the false alarm can be prevented in advance.

Further, since the angle of field of view of the light-receiver is set within 5 degrees, the size of the area for the scattered light sensing in the smoke-sensing space can be set to a requisite minimum so that the influence of the outside light can be prevented.

Further, since the light-received signal is amplified by the logarithmic amplifier, the amplified output of the light-received signal would not be saturated, and the stable fire sensing can be realized.

Further, since the light-emitting element is intermittently driven to emit light by the modulated light emission signal, and the light-received signal is amplified in synchronization with the modulated light emission signal, the illumination light or the like that would cause false alarm can be eliminated from the target of sensing, whereby the false alarm can be surely prevented from being caused by the outside light.

Further, since the light-emission pulse width is set within the range of 1 millisecond, the light emission time period can be suppressed to such a time period that the light is imperceptible for the visible sensitivity of human, whereby the blinking of the light-emitting unit of the smoke sensor can be made unrecognizable for human.

Further, since the total light emission time period at the intermittent light emission driving is set within the range of 1 millisecond, the light emission time period can be suppressed to an imperceptible range for the visible sensitivity of human, whereby the blinking of the light-emitting unit of the smoke sensor can be made unrecognizable for human.

Next, a light scattering type smoke sensor according to a second embodiment will be described. The second embodiment is basically similar to the first embodiment. The second embodiment, however, is different from the first embodiment in that the light axis of the light-emitting element and the light axis of the light-receiving element are arranged so as to intersect at a predetermined angle on the outer surface of the sensor body, since the first embodiment arranges the light axis of the light-emitting element and the light axis of the light-receiving element substantially linearly on the outer surface of the sensor body. The configuration and the method of the second embodiment are similar to those of the first embodiment if not specifically described otherwise, and the components with the similar function will be referred to by the same names or denoted by the same reference characters as the first embodiment.

FIG. 12 is a perspective view of a chamber base 41 of a smoke sensor 40 using scattering light (partly shown) according to the second embodiment. On the chamber base 41, a light-emitting opening 42 and a light-receiving opening 43 are arranged so as to intersect with each other at a predetermined angle on the outer surface of the sensor body. The light-emitting element 5 not shown is housed inside the light-emitting opening 42, whereas the light-receiving element 6 not shown is housed inside the light-receiving opening 43.

Next, a relation between light emitting angle and light receiving angle will be described in detail. It should be noted that the present application incorporates Japanese Patent Application (JP-A) No. 2002-4221 filed on Jan. 11, 2002 by the present applicant, and a part of the description below is disclosed in the JP-A 2002-4221.

FIG. 13A schematically shows an optical positional relation corresponding to the positions at which the light-emitting unit and the light-receiving unit are installed in the chamber base 41 of FIG. 12 as a representation in the three-dimensional coordinate space.

In FIG. 13A, a light axis 13 of light emission from light-emitting point O of the light-emitting element 5 is shown by a vector, and a light axis 14 of light reception along which the scattered light comes from the light axis crossing point P located in the outside open space is shown by a vector towards light-received point Q of the light-receiving element 6. Further, among the angles formed by the intersecting light axis 13 of light emission and the light axis 14 of light reception, an angle formed by light coming along the light axis 13 of light emission is scattered by smoke or the like and changes the direction so as to proceed along the light axis 14 of light reception is represented as a scattering angle θ, and a supplementary angle of the scattering angle θ is represented as a configuration angle δ (θ=180 degrees−δ).

In FIG. 13A, a triangle drawn by connecting the light-emitting point O, the light axis crossing point P, and the light-receiving point Q forms an imaginary optical plane for the smoke sensing using scattering light according to the second embodiment. The plane forming the triangle OPQ is arranged so as to form a certain angle with each of xy plane (horizontal plane) and zx plane (vertical plane).

Here, for the simplicity of description, the plane is arranged so that the projection of the light-emitting point O over the x-axis is projection point A, and an inclined angle φ formed by the light axis 13 of light emission and the vertical direction is an angle formed by the light axis 13 and the x-axis.

When the light axis 13 of light emission and the light axis 14 of light reception are viewed from the horizontal plane which is the xy plane, the projection point A corresponds to the light-emitting point O and a projection point B corresponds to the light-receiving point Q as shown in FIG. 13B. In other words, the light axis 13 of light emission and the light axis 14 of light reception intersect with each other at a predetermined angle α (apparent configuration angle α on the horizontal plane) in a horizontal direction.

When the coordinate of the light-emitting point O is set as $(a_1, b_1, c_1)$ and the coordinate of the light-receiving point Q is set as $(a_2, b_2, c_2)$, the configuration angle δ, the apparent configuration angle α on the horizontal plane, and the inclination angle φ in the vertical direction can be represented by following expressions (1) to (3):

[Expression 1]
$$\cos\delta = \frac{a_1 a_2 + b_1 b_2 + c_1 c_2}{\sqrt{a_1^2 + b_1^2 + c_1^2}\sqrt{a_2^2 b_2^2 c_2^2}} \quad \text{ex (1)}$$

[Expression 2]
$$\cos\alpha = \frac{a_1 b_1 + a_2 b_2}{\sqrt{a_1^2 + b_1^2}\sqrt{a_2^2 + b_2^2}} \quad \text{ex (2)}$$

[Expression 3]
$$\tan\phi = \frac{c_1}{a_1} \quad \text{ex (3)}$$

For example, when the inclination angle φ in the vertical direction is set to 30°, and the apparent configuration angle α on the horizontal plane is set to 120°, the configuration angle δ becomes 97°. When the apparent configuration angle α on the horizontal plane is set to 120°, and the inclination angle φ is set to 9.8°, the configuration angle δ becomes 117°.

In brief, when the apparent configuration angle α is maintained at a constant value 120°, the inclination angle φ is 9.8°, 30°, and the actual configuration angle δ is 117°, 97°. When the positions of the light-emitting point O and the light-receiving point Q in the horizontal direction are not changed, and the inclination angle φ in vertical direction is made larger, the actual configuration angle δ is made smaller on the contrary. Needless to say, when the inclination angle $\phi$ in the vertical direction is made smaller, the height of the light axis crossing point O becomes lower, and the sensor becomes thinner.

Based on the three-dimensional relation of optical axes from the light emission to the light reception as shown in FIGS. 13A and 13B, the configuration angle $\delta$ of the light axis 13 of light emission and the light axis 14 of light reception is made approximately 110° in the second embodiment. When the configuration angle $\delta$=110°, the corresponding scattering angle $\theta$ is 70°, i.e., 180°−$\delta$. The configuration angle $\delta$ is set to 110° ($\theta$=70°) for the following reasons. The smoke-sensing unit of the light scattering type smoke sensor is required to satisfy two contradictory needs: (1) to increase the amount of scattered light by smoke, and (2) to suppress the influence by the difference in the types of the smoke. The inventor found the relation between the scattering angle and the amount of scattered light for various types of smoke based on experiments and simulations (OPTIMIZATION OF SENSITIVITY CHARACTERISTICS OF PHOTOELECTRIC SMOKE DETECTOR TO VARIOUS SMOKES, Nagashima et al., Asia Oceania Fire Symposium, 1998).

Figure 14:
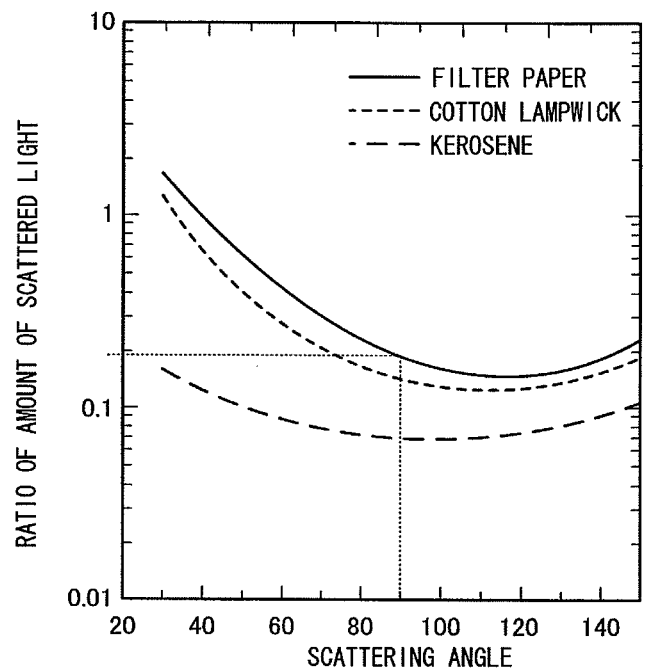
FIG. 14 shows a relation between scattering light angle and amount of scattering light for different types of smoke.
Figure 15:
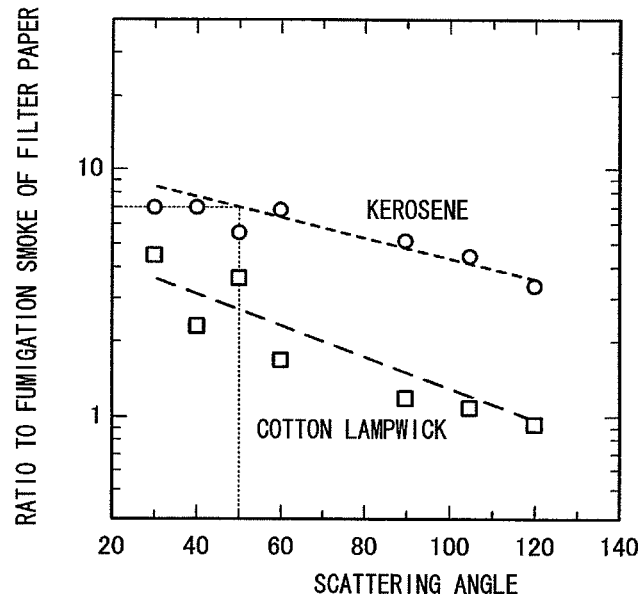
FIG. 15 shows a relation between scattering angle and ratio of amount of scattering light of kerosene combustion smoke/ cotton lampwick fumigation smoke to filter paper fumigation smoke.

FIG. 14 shows the variation in the amount of scattered light according to the scattering angle $\theta$ (=180°−$\delta$), and shows the relation between the scattering angle and the amount of scattered light for various types of smokes by a relative ratio, wherein the amount of scattered light by the fumigation smoke of the filter paper at the scattering angle=40° in the conventional light scattering type smoke sensor is set as one. As shown in FIG. 14, along with the increase in the scattering angle, the amount of scattered light decreases. For the stabilization of the operation of the smoke sensor, at least ⅕ the amount of scattered light in the conventional sensor needs to be secured, and $\theta$<90° needs to hold. On the other hand, for the suppression of influence by the types of smokes, the output of the kerosene combustion smoke needs to be larger compared with the output of the filter paper fumigation smoke shown in FIG. 15 as much as possible. The sensitivity for the kerosene combustion smoke is required to be at least ⅐ the sensitivity for the filter paper, and in this case $\theta$>50°. This is an ideal condition to pass various fire test regulated by EN standard and UL standard. The scattering angle that satisfies both standards is 50°<$\theta$<90°, and ideally, $\theta$=70°.

Thus the second embodiment attains the same effect as the first embodiment. Moreover, according to the second embodiment, when the light axis 13 of light emission of the light-emitting element 5 and the light axis 14 of light reception of the light-receiving element 6 are arranged at the configuration angle $\delta$=110°, and embedded into the chamber base 41 so that the apparent configuration angle $\alpha$ in the horizontal surface and the inclination angle $\phi$ in the vertical direction are set, even if the angular arrangement is made optimal so that there is little influence of the size of the smoke particle on the sensitivity, the amount of protrusion of the light axis crossing point P with respect to the smoke can be suppressed.

Next, a light scattering type smoke sensor according to a third embodiment will be described. The light scattering type smoke sensor according to the third embodiment is different from the light scattering type smoke sensor according to the first or the second embodiment which includes only one light-emitting element, since the smoke sensor according to the third embodiment schematically includes two light-emitting elements. The configuration and the method of the third embodiment are similar to those of the second embodiment if not specified otherwise, and the components with the similar functions are referred to by the same names or denoted by the same reference characters as the second embodiment.

First, the reason for providing two light-emitting elements is described. The conventional light scattering type smoke sensor sometimes raises false fire alarm when sensing the smoke of cooking, the steam of the bathroom, or the like, other than the smoke of fire.

It is known to direct two different types of light with different wavelengths onto the smoke-sensing space, thereby finding the ratio of light intensities of two different types of scattered light with different wavelengths to distinguish the types of the smoke, or to direct light with a vertical polarization plane and light with a parallel polarization plane with respect to the scattering plane, thereby finding the ratio of light intensities of respective polarization components of the light scattered by the smoke to distinguish the types of the smoke in order to prevent such false fire alarm from being caused by other factors than the fire.

In the conventional method of distinguishing the types of smoke using the light with different wavelengths or the light with the different polarization planes, however, the accuracy of distinction between the smoke of fire and the smoke of non-fire, such as steam of cooking and the steam of a bathroom is not sufficient. Hence, a more highly accurate smoke distinction is desirable.

Hence, in the third embodiment, in addition to the elimination of the smoke chamber in the smoke sensor for realization of a thinner and smaller smoke sensor, one of the objects is improvement in accuracy of smoke distinction for realization of secure prevention of non-fire alarm.

Figure 16:
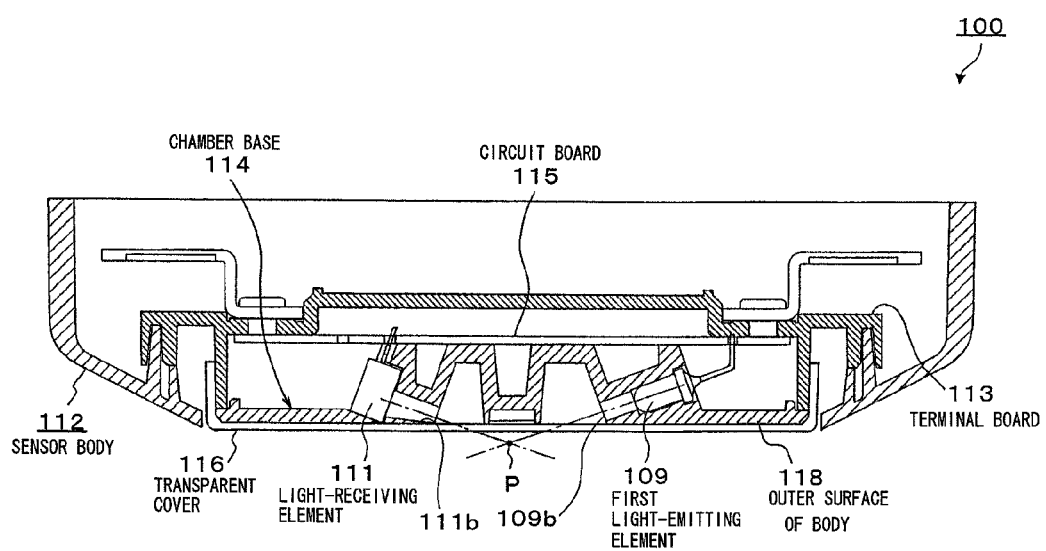
FIG. 16 is a sectional view of a light scattering type smoke sensor according to a third embodiment.

Next, the light scattering type smoke sensor according to the third embodiment will be described. FIG. 16 is a sectional view of the light scattering type smoke sensor according to the third embodiment. The smoke sensor 100 using scattering light schematically includes a sensor body 112, a terminal board 113, a chamber base 114, a first light-emitting element 109, a second light-emitting element 110 (not shown in FIG. 16), a light-receiving element 111, and a transparent cover 116. If not specified otherwise, the sensor body 112, the terminal board 113, the chamber base 114, the first light-emitting element 109, the light-receiving element 111, and the transparent cover 116 can be configured similarly to the sensor body 2, the terminal board 3, the chamber base 4, the light-emitting element 5, the light-receiving element 6, and the transparent cover 9, and the second light-emitting element 110 can be configured similarly to the light-emitting element 5.

Here, the first light-emitting element 109 and the second light-emitting element 110 as plural light emitters, and the light-receiving element 111 as the light receivers are housed in the chamber base 114. Further, two light-emitting openings 109b, 110b (only one light emitting opening 109b is shown in FIG. 16) for ejecting the light emitted from the first light-emitting element 109 and the second light-emitting element 110 to the outside of the smoke sensor 100 using scattering light, and a light receiving opening 111b for introducing the light thus ejected and scattered by the smoke into the light-receiving element 111 are formed in an outer surface 118 of the sensor body. In the outside open space further below the outer surface 118 of the sensor body, light axis crossing point P where the light axes of the first light-emitting element 109 and the second light-emitting element 110 intersect with the light axis of the light-receiving element 111 is set, and the light axis crossing point P forms the smoke-sensing point.

When the sensor base (not shown) which is the base for the attachment of the smoke sensor 100 using scattering light is installed on the ceiling surface (not shown) and the smoke sensor 100 using scattering light shown in FIG. 16 is attached to the sensor base, there is no protruding portion of the smoke chamber similarly to the first embodiment shown in FIG. 2A, whereby the smoke sensor 100 using scattering light can be installed to the ceiling surface in such a manner that the smoke sensor 100 does not stand out.

Further, when the sensor base is installed inside the ceiling surface and the smoke sensor 100 using scattering light of FIG. 16 is embedded and attached to the sensor base, similarly to the first embodiment of FIG. 2B, the lower surface of the smoke sensor 100 using scattering light is coplanar with the ceiling surface and there is no protruding portion, whereby the full-flat ceiling configuration can be realized. Particularly, the portion to be embedded in the ceiling surface becomes smaller than in the conventional sensor, whereby the smoke sensor 100 using scattering light can be arranged to the narrow ceiling space.

Figure 17:
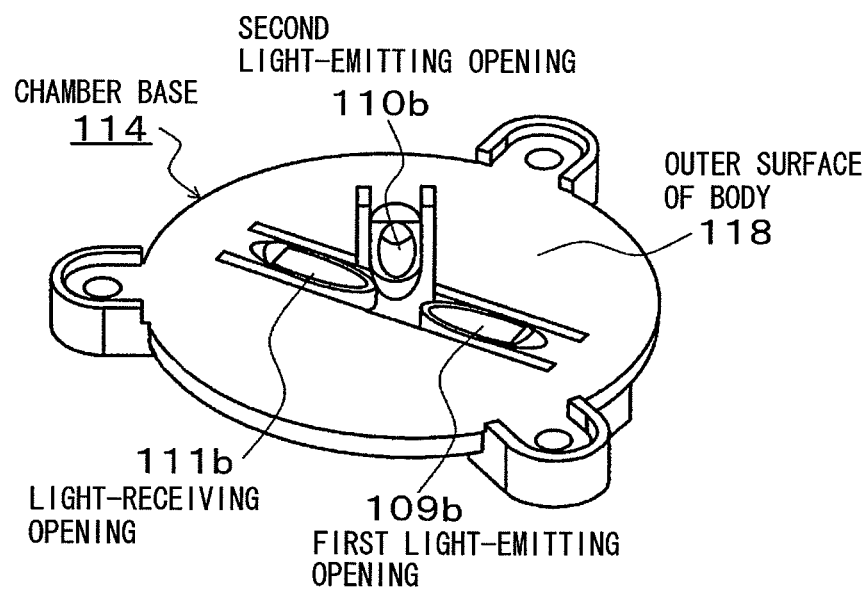
FIG. 17 is a perspective view of a chamber base.

FIG. 17 is a perspective view of the chamber base 114 which is employed for the solid-angle arrangement of the first light-emitting element 109, the second light-emitting element 110, and the light-receiving element 111. In FIG. 17, the first light-emitting opening 109b, the second light-emitting opening 110b, and the light-receiving opening 111b are formed on the outer surface 118 of the chamber base 114, and the first light-emitting element 109, the second light-emitting element 110, and the light-receiving element 111 are embedded inside respective openings (those elements are not shown in FIG. 17).

FIG. 18 is a sectional view of the entire smoke-sensing unit in the solid-angle arrangement in which the chamber base 114 of FIG. 17 is employed (sectional view along the section passing through the first light emitting-opening 109b and the light-receiving opening 111b. The transparent cover 116 is shown by an imaginary line). In FIG. 18, an upper portion of the chamber base 114 is formed as the flat outer surface 118 of the sensor body, and the first light-emitting opening 109b, the second light-emitting opening 110b, and the light-receiving opening 111b are formed therein, with the transparent cover 116 attached for protection.

The first light-emitting element 109, the second light-emitting element 110 (not shown in FIG. 18), and the light-receiving element 111 are embedded inside the chamber base 114, and the light axis 109a of the first light-emitting element 109, the light axis 110a of the second light-emitting element 110 (not shown in FIG. 18), and the light axis 111a of the light-receiving element 111 form a solid crossing with each other at the smoke-sensing point P in the open smoke-sensing space outside the outer surface 18 of the sensor body.

Here, the height h from the outer surface 118 of the sensor body to the smoke-sensing point P which is the light axis crossing point in the outside space may be set to such a height that the substance adhering to the outer surface 7 of the sensor body does not affect the smoke sensing similarly to the first embodiment. Preferably, h is set to a height equal to or longer than 5 mm, for example.

Figure 19:
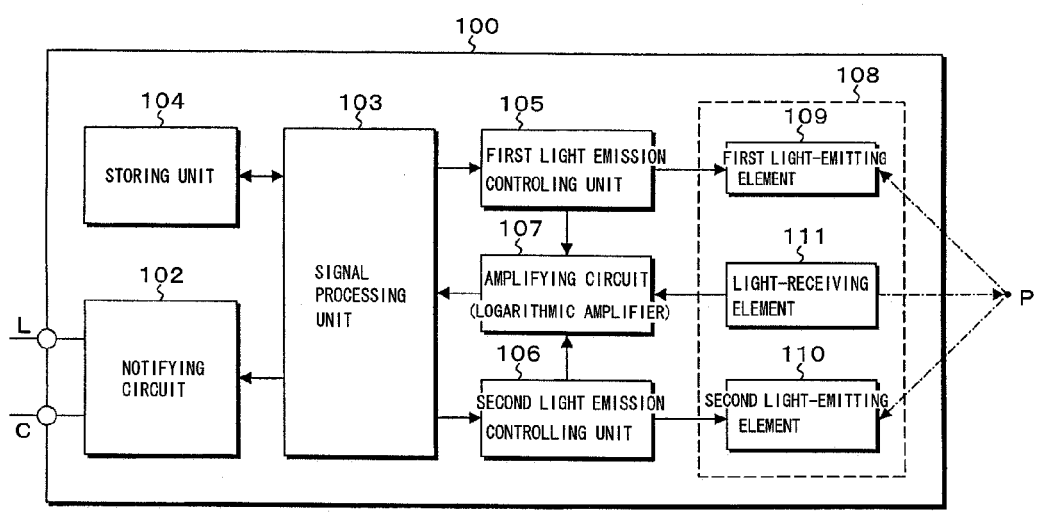
FIG. 19 is a circuit block diagram of the light scattering type smoke sensor according to the third embodiment.

FIG. 19 is a circuit block diagram of the light scattering type smoke sensor according to the third embodiment. In FIG. 19, the smoke sensor 100 using scattering light includes a notifying circuit 102, a signal processing unit 103 using a micro processing unit (MPU), a storing unit 104, a first light emission controlling unit 105, a second light emission controlling unit 106, an amplifying circuit 107, and a smoke-sensing unit 108. If not specified otherwise, the notifying circuit 102, the signal processing unit 103, the storing unit 104, the first light emission controlling unit 105, the amplifying circuit 107, and the smoke-sensing unit 108 can be similarly configured as the notifying circuit 15, the signal processing unit 16, the storing unit 17, the light emission controlling unit 18, the amplifying circuit 19, and the smoke-sensing unit 4a, and the second light emission controlling unit 106 can be similarly configured as the light emission controlling unit 18.

The smoke-sensing unit 108 includes the first light-emitting element 109, the second light-emitting element 110, and the light-receiving element 111. The first light-emitting element 109, the second light-emitting element 110, and the light-receiving element 111 are arranged so that the light axes thereof intersect with each other at the smoke-sensing point P set in the open space outside the smoke sensor.

FIG. 20A shows the solid-angle arrangement of light axes 109a and 110a for light emission of the first light-emitting element 109 and the second light-emitting element 110, and a light axis 111a for light reception of the light-receiving element 111.

The smoke-sensing point P where the light axes 109a and 110a of light emission and the light axis 111a of light reception intersect with each other exists in the open smoke-sensing space outside the outer surface 118 of the sensor body of the chamber base 114 of FIG. 17, whereas the first light-emitting element 109, the second light-emitting element 110, and the light-receiving element 111 are arranged inside the chamber base 114.

FIG. 20B shows the solid-angle arrangement of point A of the first light-emitting element 109 and point C of the light-receiving element 111. Here, a plane including the light axis 109a of light emission from the point A of the first light-emitting element 109 and the light axis 111a of light reception from the point C of the light-receiving element 111 is represented by triangle PCA, and an angle formed by the light axis 109a of light emission and the light axis 111a of light reception in the plane including the triangle PCA is a first scattering angle $\theta 1$ of the first light-emitting element 109.

FIG. 20C shows the solid-angle arrangement of point B of the second light-emitting element and point C of the light-receiving element 111. Here, the light axis 110a of light emission and the light axis 111a of light reception exist in the plane including the triangle PCB, and the scattering angle formed by the light axis 110a of light emission and the light axis 111a of light reception is represented as a scattering angle $\theta 2$ which is formed by the light axis 110a of light emission and the light axis 111a of light reception in the plane including the triangle PCB.

Figure 21:
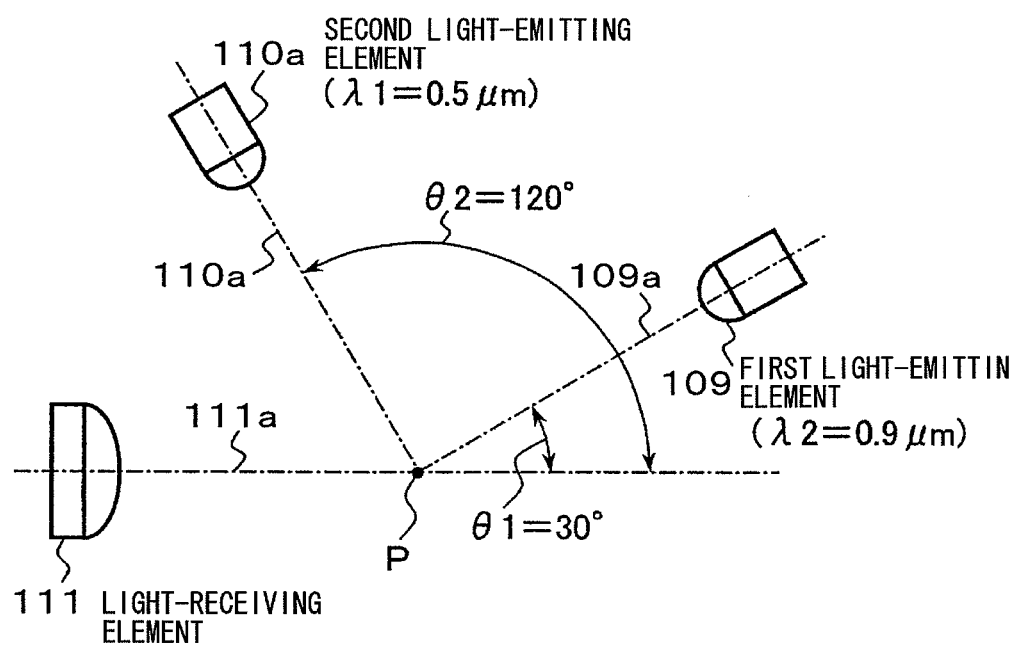
FIG. 21 shows relation of locations of the first light-emitting element, the second light-emitting element, and the light-receiving element when the light axes thereof are assumed to be on a same plane.

For the simplicity of description of the configuration of the smoke-sensing unit 108 having the solid-angle arrangement of FIGS. 20A to 20C, it is assumed that the light axes of the first light-emitting element 109, the second light-emitting element 110, and the light-receiving element 111 exist in the same plane as shown in FIG. 21.

In FIG. 21, the first light-emitting element 109 is set so as to have the first scattering angle $\theta 1$ as $\theta=30°$, wherein the first scattering angle $\theta 1$ is formed by the light axis 109a of light emission of the first light-emitting element 109 and the light axis 111a of light reception of the light-receiving element 111 with respect to the crossing point P thereof in the third embodiment. Further, a near infrared light emitting diode (LED) is employed as the first light-emitting element 109, and the light emitted from the first light-emitting element 109 is set so that the central wavelength is $\lambda 1=900$ nm ($=0.9$ μm) in the third embodiment.

In the third embodiment, in addition to the first light-emitting element 109, the second light-emitting element 110 is provided. The second light-emitting element 110 is set so that the second scattering angle $\theta 2$ formed by the light axis 110a of light emission of the second light-emitting element 110 and the light axis 111a of light reception of the light-receiving element 111 with respect to the crossing point P thereof is larger than the first scattering angle θ1 of the first light-emitting element 109 and the light-receiving element 111 (θ2>θ1). In the third embodiment, the second scattering angle θ2 is set to 120°.

A visible light LED is employed for the second light-emitting element 110. When the central wavelength of the light emitted from the second light-emitting element 110 is referred to as second wavelength λ2, the wavelength λ2 is set shorter than the wavelength λ1 of the first light-emitting element 109. In the third embodiment, λ2=500 nm (=0.5 μm).

Further, it is desirable that a laser diode which emits collimated parallel beam be employed as the first light-emitting element 109 and the second light-emitting element 110. Further, an element with a narrower angle of field of view with respect to the smoke-sensing point P is preferably used as the light-receiving element 111. The angle of field of view is, for example, not more than 5 degrees. When the angle of field of view is set to such range, the light from only the restricted smoke-sensing space around the smoke-sensing point P is received, and the amount of disturbing light other than the scattered light of smoke incident on the light receiving unit can be reduced and the influence by the outside light can be minimized. With this configuration, the light scattering type smoke sensor can reduce the risk of false alarm by the disturbing light, such as the illumination light or the reflected light of sunlight. Further, since the amount of received disturbing light can be suppressed, the risk of the amplifying circuit 107 of FIG. 19 reaching the saturated level can be reduced.

Figure 22:
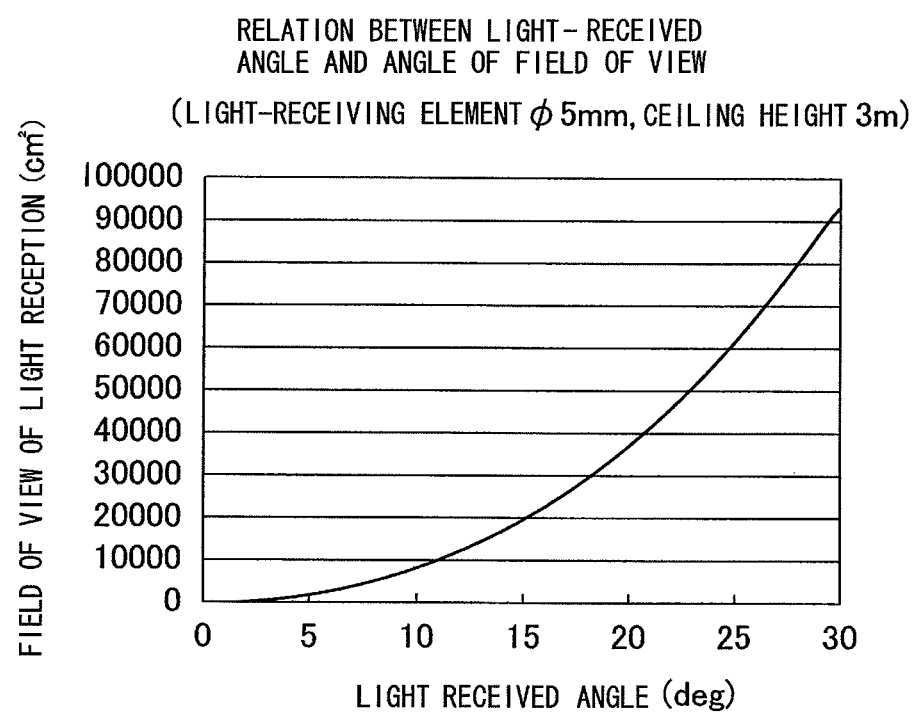
FIG. 22 shows a relation between angle of field of view and area of field of view.

FIG. 22 shows a relation between the angle of field of view and the area of field of view, wherein the horizontal axis represents the angle of field of view of the light scattering type smoke sensor when the light scattering type smoke sensor is installed on the ceiling surface of the height of approximately 3 m for monitoring, and the vertical axis represents the area (area of field of view) of the floor surface included in the field of view of the light scattering type smoke sensor. As shown in FIG. 22, when the angle of field of view is 5 degrees, the area of field of view is approximately 2200 cm$^2$, whereas when the angle of field of view is 20 degrees, the area of field of view is approximately 38000 cm$^2$. Then the amount of received disturbing light increases by the area ratio if the illumination light or the like in the room is uniform, and along with the increase in the angle of field of view, the risk of the amplifying circuit 107 of FIG. 19 reaching the saturated level dramatically increases in a manner of quadric function.

Further, though it is preferable that the angle of field of view of the light-receiving unit be narrow for the reduction of influence of the disturbing light, when a lens-attached photodiode or a phototransistor is employed as the light-receiving element 111, it is prerequisite that the angle of field of view is not more than 5 degrees. On the other hand, when the angle of field of view is narrower than is required, the amount of received light of the scattered light of smoke itself becomes small, whereby the S/N ratio is degraded. Hence, the angle of field of view of the light-receiving unit is preferably not more than 5 degrees.

Figure 23:
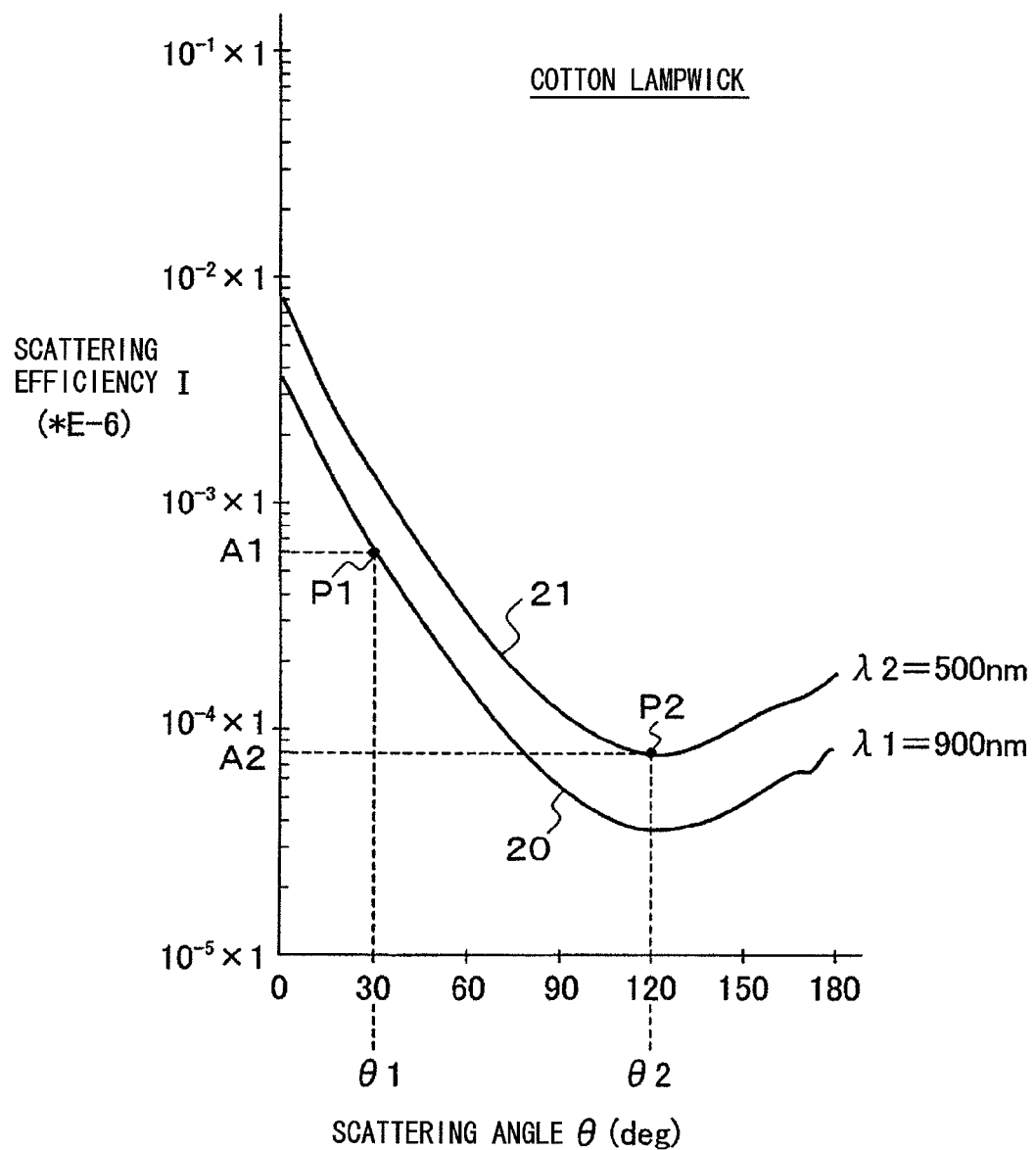
FIG. 23 is a graph of scattering efficiency I against scattering angle θ for fumigation smoke generated by combustion of the cotton lampwick.

FIG. 23 is a graph of scattering efficiency I of the light from the first light-emitting element 109 and the second light-emitting element 110 by the fumigation smoke (white smoke) generated by the combustion of cotton lampwick against the scattering angle θ, which is observed in the smoke-sensing unit with the configuration as shown in FIGS. 16 to 21. The horizontal axis in FIG. 23 represents the scattering angle θ (where θ=0°~180°), and the vertical axis represents the scattering efficiency I in the logarithmic coordinate.

When the light emitted from the first light-emitting element 109 has the first wavelength λ1=900 nm, the scattering efficiency at the side of the light-receiving element 111 appears as a characteristic curve 20. On the other hand, when the light emitted from the second light-emitting element 110 has the second wavelength λ2=500 nm, the scattering efficiency at the side of the light-receiving element 111 appears as a characteristic curve 21.

When the characteristic curves 20 and 21 are examined with respect to the wavelength of the light emitted from the light-emitting element, it can be seen that the characteristic curve 13 of the wavelength λ1=900 nm of the first light-emitting element 109 has a lower scattering efficiency, whereas the characteristic curve 14 of the shorter second wavelength λ2=500 nm of the second light-emitting element 110 has a higher scattering efficiency.

On the other hand, with respect to the variation in the scattering angle θ of the characteristic curves 20 and 21 of the scattering efficiency of the first and the second light-emitting elements 109 and 110, both shows a higher scattering efficiency for the smaller scattering angle θ, and the scattering efficiency decreases along with the increase in the scattering angle. The scattering efficiency hit the lowest value when the scattering angle is approximately 120°. Then, along with the increase in the scattering angle, the scattering efficiency increases.

In the third embodiment, the scattering angle θ1 of the first light-emitting element 109 is set to 30°, whereby the scattering efficiency A1 is obtained at the point P1 in the characteristic curve 20. On the other hand, with respect to the second light-emitting element 110, the second scattering angle θ2 is set to 120°, whereby the scattering efficiency A2 is obtained at the point P2 in the characteristic curve 21.

When the first light-emitting element 109 and the second light-emitting element 110 emit light of different wavelengths at different scattering angles, the resulting scattering efficiency is as described above. Then, the amount of received light of the light-receiving element 111 can be represented as (amount of received light)=(amount of emitted light)×(light-received efficiency), whereby the amount of light-received signal is in direct proportion to the scattering efficiency I of FIG. 23.

In the third embodiment, ratio R is found; the ratio R is the ratio of the amount of light received by the light-receiving element 111 when the light emitted from the first light-emitting element 109 is scattered by smoke to the amount of light received by the light-receiving element 111 when the light emitted from the second light-emitting element 110 is scattered by the same type of smoke. Since the ratio R of the amount of received light is in direct proportion to the scattering efficiency, when the scattering efficiency is represented as A1 and A2, R can be found as R=A1/A2. Through the comparison of the ratio R with the predetermined threshold, the type of the smoke can be decided.

Figure 24:
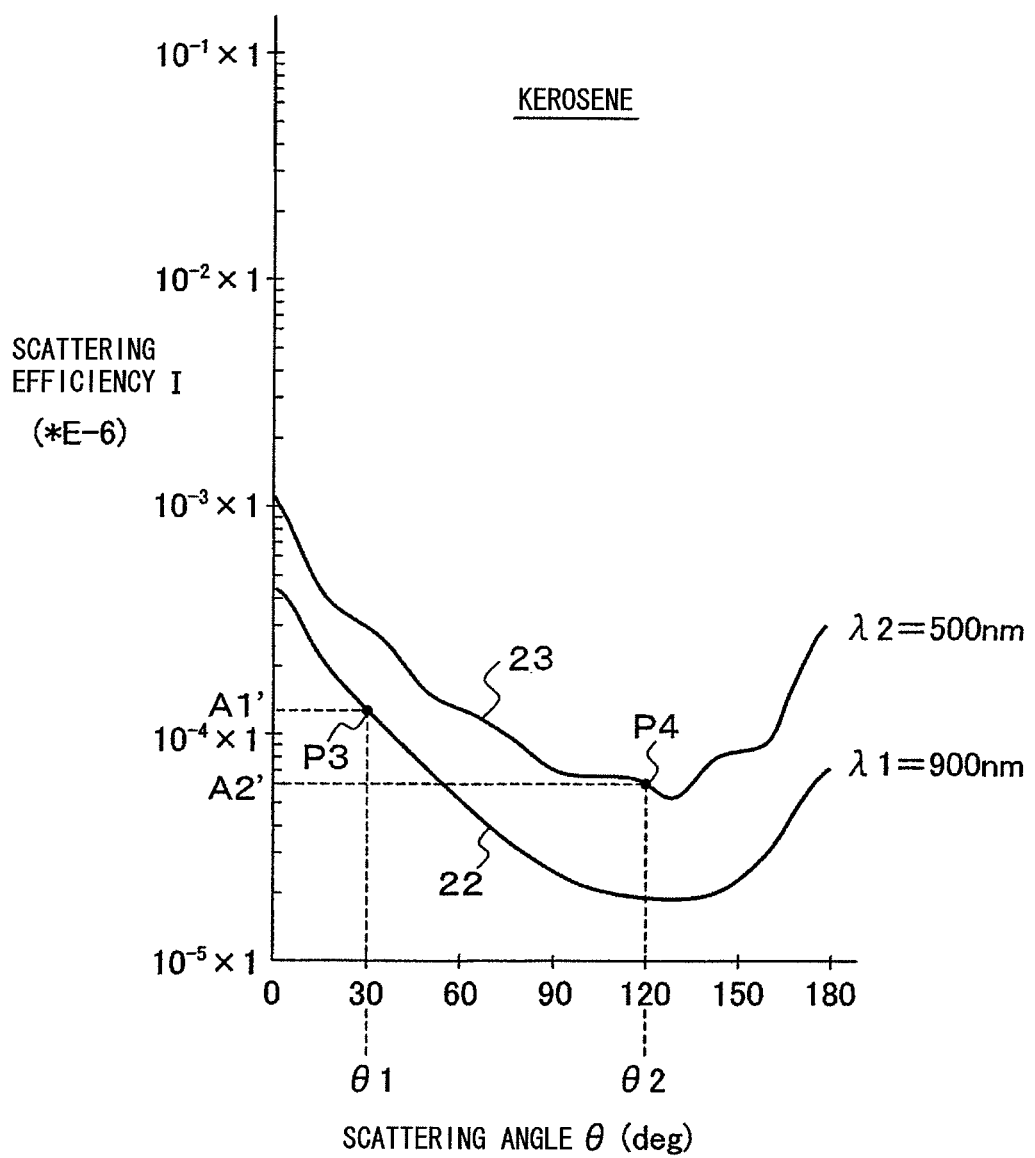
FIG. 24 is a graph of scattering efficiency I against scattering angle θ for combustion smoke generated by combustion of kerosene.

FIG. 24 is a graph of the scattering efficiency I against the scattering angle θ, which is obtained when the light emitted from the first light-emitting element 109 and the light emitted from the second light-emitting element 110 are scattered by the combustion smoke (black smoke) generated by the combustion of kerosene when the smoke-sensing unit has the configuration shown in FIGS. 16 to 21.

In FIG. 24, when the light emitted from the first light-emitting element 109 has the first wavelength λ1=900 nm, the scattering efficiency I of the light can be represented as a characteristic curve 22. On the other hand, when the light emitted from the second light-emitting element 110 has the second wavelength $\lambda 2=500$ nm, the scattering efficiency I of the light can be represented as a characteristic curve 23.

When the wavelength is focused in the graph of FIG. 24, similarly to the smoke of cotton lampwick of FIG. 23, the characteristic curve 22 takes low values, whereas the characteristic curve 23 takes higher values, wherein the characteristic curve 22 shows the scattering efficiency of the light emitted from the first light-emitting element 109 and the light has the first wavelength $\lambda 1=900$ nm, and the characteristic curve 23 shows the scattering efficiency of the light emitted from the second light-emitting element 110 and the light has the shorter second wavelength $\lambda 2=500$ nm.

Further, the variation in the scattering efficiency against the scattering angle $\theta$ is similar to the case of FIG. 23. In both the characteristic curves 22 and 23, the scattering efficiency becomes high as the scattering angle $\theta$ decreases. The scattering efficiency hits the minimum value when the scattering angle $\theta$ is approximately 120°, then the scattering efficiency increases along with the increase in the scattering angle $\theta$.

With respect to the combustion smoke of kerosene, when the first scattering angle $\theta 1$ of the first light-emitting element 109 is 30° in the characteristic curve 22, the scattering efficiency is A1' at point P3. Further, with respect to the second light-emitting element 10, since the second scattering angle $\theta 2$ is 120°, the scattering efficiency is A2' at point P4 in the characteristic curve 23.

Similarly to the case of FIG. 23, the scattering efficiencies A1' and A2' is in direct proportion to the amount of received light, i.e., product of the amount of emitted light and the light-received efficiency. Hence, the ratio R, which is the ratio of the amount of light emitted from the first light-emitting element 109 and received by the light-receiving element 111 to the amount of light emitted from the second light-emitting element 110 and received by the light-receiving element 111, is found as R=A1'/A2' based on the scattering efficiencies A1' and A2'.

FIG. 25 shows a list of the amount of light-received signal A1 for the first light-emitting element 109, the amount of light-received signal A2 for the second light-emitting element 110, and the ratio R of the amount of signals, with respect to the fumigation smoke of the cotton lampwick and the combustion smoke of the kerosene, by way of example. Here, since the amount of light-received signal is in direct proportion to the scattering efficiency, the values of the scattering efficiency I of FIGS. 23 and 24 are shown as they are.

As is clear from the list of FIG. 25, with respect to the fumigation smoke, which appears to be white smoke, generated by the combustion of the cotton lampwick, the ratio R of the amount of light-received signals for the light from the first light-emitting element 109 and the light from the second light-emitting element 110 is 8.0.

On the other hand, with respect to the combustion smoke, which appears to be black smoke, generated by the combustion of kerosene, the ratio R of the amount of light-received signals for the light from the first light-emitting element 109 and the light from the second light-emitting element 110 is 2.3.

Hence, with respect to the white fumigation smoke and the black combustion smoke, there is a sufficient difference between the ratios of the amounts of light-received signals for the light from the first light-emitting element 109 and for the light from the second light-emitting element 110. If the ratio R is to be employed as a threshold for deciding the type of the smoke, the threshold may be set to 6, so that the smoke generated at the fire occurrence can be decided to be the fumigation smoke or the combustion smoke.

On the other hand, the water vapor or the steam have sufficiently larger particle diameter compared with the smoke particle. Hence, the scattering efficiency is sufficiently higher than that of the smoke from fire when the scattering angle $\theta$ is small in FIGS. 23 and 24, and the amount of light-received signal for the light from the first light-emitting element 109 at the first scattering angle $\theta 1$ is sufficiently large, so that the ratio R of the amount of light-received signal for the light from the first light-emitting element 109 at the first scattering angle $\theta 1$ to the amounts of light-received signal for the light from the second light-emitting element 110 at the second scattering angle $\theta 2=120°$ takes a large value of 10 or more.

Hence, it is possible to set the threshold to 10 with respect to the ratio R of the amount of light-received signal for the light from the first light-emitting element 109 to the amount of light-received signal for the light from the second light-emitting element 110, and to decide that the smoke is not from fire but from water vapor or steam when the ratio R is above the threshold.

The same applies to the smoke of tobacco. Since the ratio R is 10 or more for the smoke of tobacco, if the threshold for the ratio R is set to 10, and the ratio is above the set threshold, smoke can be similarly decided as being caused by non-fire.

FIG. 26 is a flowchart of the fire sensing process by sensor with the circuit block of FIG. 19 having the smoke-sensing unit of FIGS. 16 to 21, and the fire sensing process is realized by programmed control of CPU which functions as the signal processing unit 103.

In the fire sensing process, only the first light-emitting element 109 is driven to emit light in the normal operation. When the level of received light from the first light-emitting element 109 exceeds a predetermined threshold which serves like a pre-alarm, the sensor drives the second light-emitting element 110 to emit light and decides whether the fire occurs or not based on the ratio of the amounts of receive light signals for the light from the first light-emitting element 109 and for the light from the second light-emitting element 110.

In FIG. 26, first the counter n is set as n=1 in step SB1. Then, in step SB2, the first light-emitting element 109 is driven to emit light like pulses. In step SB3, in response to the light emission driving of the first light-emitting element 9, the light-received signal of the light-receiving element 111 is sampled and held, and light-received data A1 is stored in the storing unit 104. Simultaneously, the differential value B is found for the light-received data A1 and stored in the storing unit 104.

The first light emission controlling unit 105 of FIG. 19, similarly to the first embodiment shown in FIG. 6, performs modulated light emission by driving the first light-emitting element 109 to emit light as light-emission pulses so that pulse width T2 is output repeatedly every cycle T1. Accordingly the amplifying circuit 107 takes in the light-received signal as a synchronous light-received signal which is in synchronization with the light emission modulation.

The light-emission cycle T1 is, for example, 1 second, and the pulse width T2 of the modulated light emission is, for example, 500 microseconds. The modulated light emission and corresponding synchronous light reception allow for the elimination of light-received signal generated by the incidence of light other than the scattered light by the smoke in the smoke-sensing space outside, and secure the reception of only the scattered light of the smoke.

Further, since the light emission wavelength band of the first light-emitting element 109 is in a visible light band, the light emission time period is restricted to 1 millisecond or less so that the human cannot visually recognize the intermittently emitted light. For the human to visually recognize the light from the light-emitting element, the light emission must continue for more than 1 millisecond. Hence, the light emission time period is restricted to 1 millisecond or less so that the human cannot visually recognize the light from the light-emitting element.

In case of the modulated light-emission pulse, it is sufficient if the total light emission time period of three light-emission pulses is 1 millisecond or less. In this case the total light emission time period is 150 microseconds, so that the light emission is not visually recognized. The modulated light emission and the synchronous light reception are similar for the light emission control of the second light-emitting element 110 by the second light emission controlling unit 106 of FIG. 19.

Returning again to FIG. 26, it is checked whether the light-received data A1 exceeds the predetermined threshold TH1 or not in step SB4, the predetermined threshold TH1 serves for judgment on a pre-alarm of the fire. When the light-received data A1 exceeds the threshold, the obstacle judgment process of step SB5 described later is performed. When the smoke is decided as not from non-fire, the second light-emitting element 110 is driven to emit light as pulses in step SB6, and the light-received signal obtained from the light-receiving element 110 is sampled and held in step SB7, and stored as light-received data A2 in the storing unit 104.

Then, the ratio R is calculated in step SB8, wherein the ratio R is the ratio of the light-received data A1 for the light from the first light-emitting element 109 stored in the storing unit 104 to the light-received data A2 for the light from the second light-emitting element 110 stored in the storing unit 104. Then, the ratio R is compared with the predetermined threshold=10 for deciding whether the smoke is from non-fire or not in step SB9. When the ratio R is smaller than the threshold=10, the smoke is decided as from fire, and the ratio R is compared with the threshold=6 for deciding the type of the combustion material in step SB10.

Here, if the ratio R is equal to or more than the threshold=6, the fire causing the smoke is decided to be the white smoke fire (fumigation fire) in step SB11. In step SB12, the count n of the counter is incremented by one, and in step SB13 it is checked whether the count n of the counter reaches 3 or not.

Since the count n of the counter is 2, the process returns to step SB2, to repeat the process from step SB2 to SB12. When the count n of the counter reaches 3 in step SB13, the smoke is decided to be from fire in step SB15. Then the fire signal is sent. If necessary, information indicating that the fire is white smoke fire is sent simultaneously.

On the other hand, when the ratio R is less than the threshold=6 in step SB10, the process proceeds to step SB14, and the smoke is decided to be from the black smoke fire (combustion fire). In step SB15 the smoke is decided to be from fire and the fire signal is sent to the receiver side. If necessary, the information indicating that the fire is black smoke fire is sent simultaneously. When the ratio R is equal to or higher than the threshold 10 in step SB9, the smoke is decided to be from non-fire in step SB16, and the process returns to step SB1. The counter is reset to n=1.

Thus, in the third embodiment, lights with different wavelengths and different scattering angles are emitted from the first light-emitting element 9 and the second light-emitting element 10 in the smoke-sensing unit of FIGS. 16 to 21. The lights are received by the light-receiving element 11 and the ratio of the two is found and compared with the predetermined threshold. Based on the comparison, it is decided whether the smoke is from fire or from non-fire. Further, when the smoke is decided to be from fire, the type of the combustion material, i.e., whether the fire is the white smoke fire or the black smoke fire can be surely decided.

Here, in the smoke-sensing unit with the configuration of FIGS. 16 to 21, the first wavelength $\lambda 1$ is set to 900 nm, and the first scattering angle $\theta 1$ is set to 30° for the first light-emitting element 109, and the second wavelength $\lambda 2$ is set to 500 nm, and the second scattering angle $\theta 2$ is set to 120° for the second light-emitting element 110, by way of example. In the third embodiment, though the optimal values are as above, the values of the following range can realize the same effect.

First, the first wavelength $\lambda 1$ of the first light-emitting element 109 may have a central wavelength of 800 nm or more. The first scattering angle $\theta 1$ of the first light-emitting element 109 may be in the range of $\theta 1=20°$ to 50°. On the other hand, the second wavelength $\lambda 2$ of the second light-emitting element 110 may have the central wavelength of 500 nm or less, and the second scattering angle $\theta 2$ may be in the range of $\theta 2=100°$ to 150°.

More specifically, the first wavelength $\lambda 1$ and the scattering angle $\theta 1$ of the first light-emitting element 109 and the second wavelength $\lambda 2$ and the scattering angle $\theta 2$ of the second light-emitting element 110 may be set so that the ratio R of the amounts of received light from respective elements is higher than the threshold=6 for distinction of the combustion material with respect to the smoke of the cotton lampwick of FIG. 23, i.e., the fumigation smoke (white smoke), whereas the ratio R of the amount of received light, i.e., the ratio of light emitted by the first light-emitting element 109, scattered by the smoke, and received to the amount of light emitted by the second light-emitting element 110, scattered by the smoke, and received, may be set smaller than the threshold=6 with respect to the combustion smoke of kerosene of FIG. 25, i.e., the combustion smoke (black smoke).

Further, in the signal processing unit 3 of FIG. 19, inherent false alarm caused by the setting of the smoke-sensing point P in the open smoke-sensing space outside the outer surface 118 of the sensor body is distinguished and the obstacle signal is output.

The inherent false alarm caused by the setting of the smoke-sensing point P outside is, for example, expected to be generated by the foreign substances, such as the person's hand or the insects, directly passing over the smoke-sensing point P. Hence in the process of FIG. 26, the obstacle judgment process is provided in step SB5, and the content of the processing is as shown in the flowchart of FIG. 27.

Figure 27:
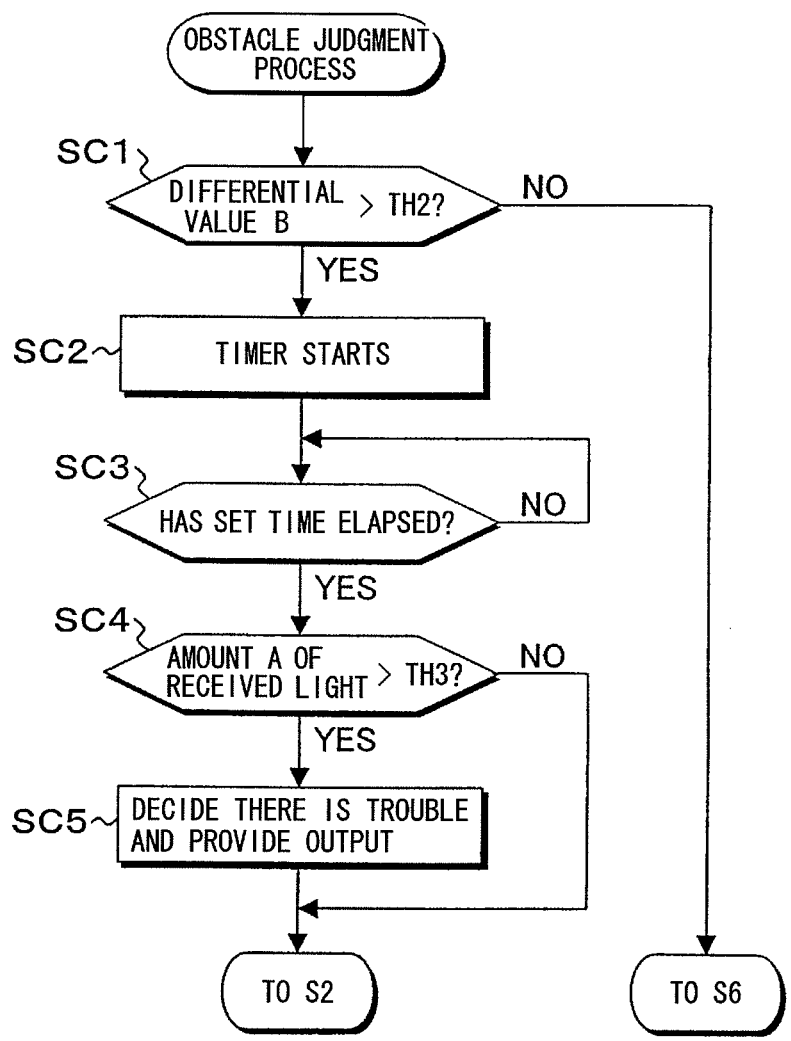
FIG. 27 is a flowchart of an obstacle judgment process of FIG. 26.

In the obstacle judgment process of FIG. 27, first it is checked whether the differential value B of the light-received data A1 exceeds the predetermined obstacle threshold TH2 or not in step SC1. When the differential value B does not exceed the predetermined obstacle threshold TH2, the process proceeds to step SB6 of FIG. 26, and the fire judgment process is performed.

When the differential value B exceeds the obstacle threshold TH2, the predetermined time T is set to the timer and the timer starts in step SC2. In step SC3, the elapse of the set time T is monitored. When the set time T has elapsed, the process proceeds to step SC4, and it is checked whether the light-received data A1 at the time exceeds the obstacle threshold TH3 or not. When the light-received data A1 exceeds the obstacle threshold TH3, it is decided that the foreign substances such as spider's nest adheres to the smoke detecting portion of the outer surface 118 of the sensor body, and the presence of trouble is notified as an output in step SC5. Then, the receiver makes the display indicating the obstacle, so as to prompt the maintenance check, such as cleaning, of the outer surface of the sensor body.

Similarly to FIG. 8 of the first embodiment, the increase in the smoke concentration by the fire is relatively mild. Hence, the differential value B is sufficiently small compared with the false alarm threshold TH2, and does not exceeds the false alarm threshold TH2 when fire occurs. Therefore, when the light-received data A1 exceeds the pre-alarm threshold TH1 at time t1, the differential value B is lower than the false alarm threshold TH2, which is decided in step SC1 of FIG. 27. Then, the obstacle judgment process of steps SC2 to SC5 is skipped, and the process proceeds to the fire judgment process after step SB6 of FIG. 26. Here, the obstacle threshold TH3 is set at a sufficiently high level compared with the pre-alarm threshold TH1 for fire judgment.

Figure 28:
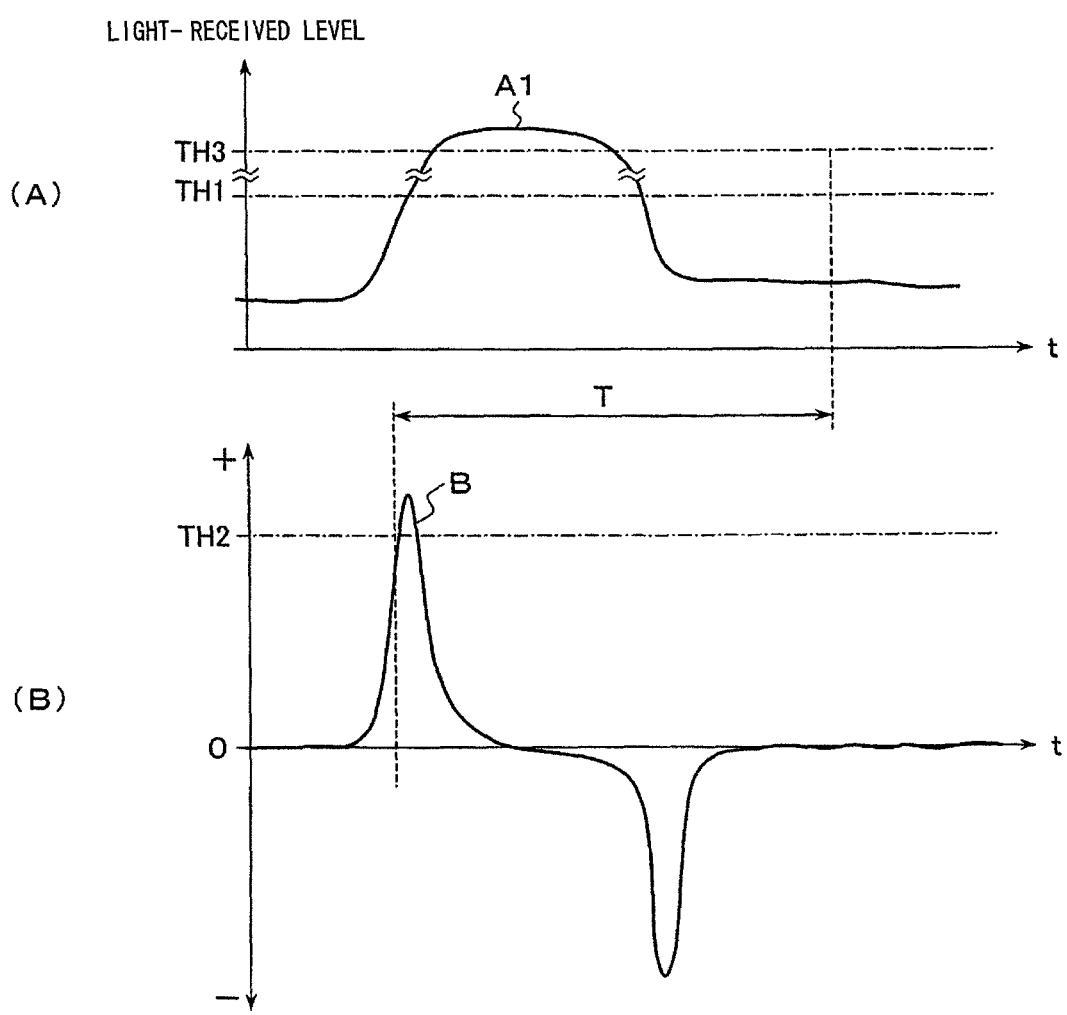
FIG. 28 is a time chart of a temporal increase in scattering light.

FIG. 28 shows a case where a foreign substance such as an insect temporarily passes over the portion of the smoke-sensing point P in the outside open space outside the outer surface 118 of the sensor body. The light-received data A1 changes so as to temporarily exceed the obstacle threshold TH3. Along with the change in the light-received data A1, the differential value B changes to a positive direction so as to exceed the false alarm threshold TH2 at the rising of the light-received data A1, and further the differential value B changes significantly to a negative direction at the falling of the light-received data A1.

A predetermined value B which is stored immediately before the time the light-received data A1 exceeds the obstacle threshold TH3 is compared with the false alarm threshold TH2. When the predetermined value B exceeds the false alarm threshold TH2, it is decided that there is a possibility of obstacle. In order to check the subsequent changes, the timer is activated when the differential value B exceeds the obstacle threshold TH2, and the sensor stands by until the set time T elapses.

Then, the light-received data A1 is checked again after time T elapses. Since the light-received data A1 is equal to or less than the obstacle threshold TH3, the obstacle is decided to be temporal. Since the obstacle is already removed, no output is provided to indicate the obstacle. In other words, the execution of the fire judgment process is suppressed.

Figure 29:
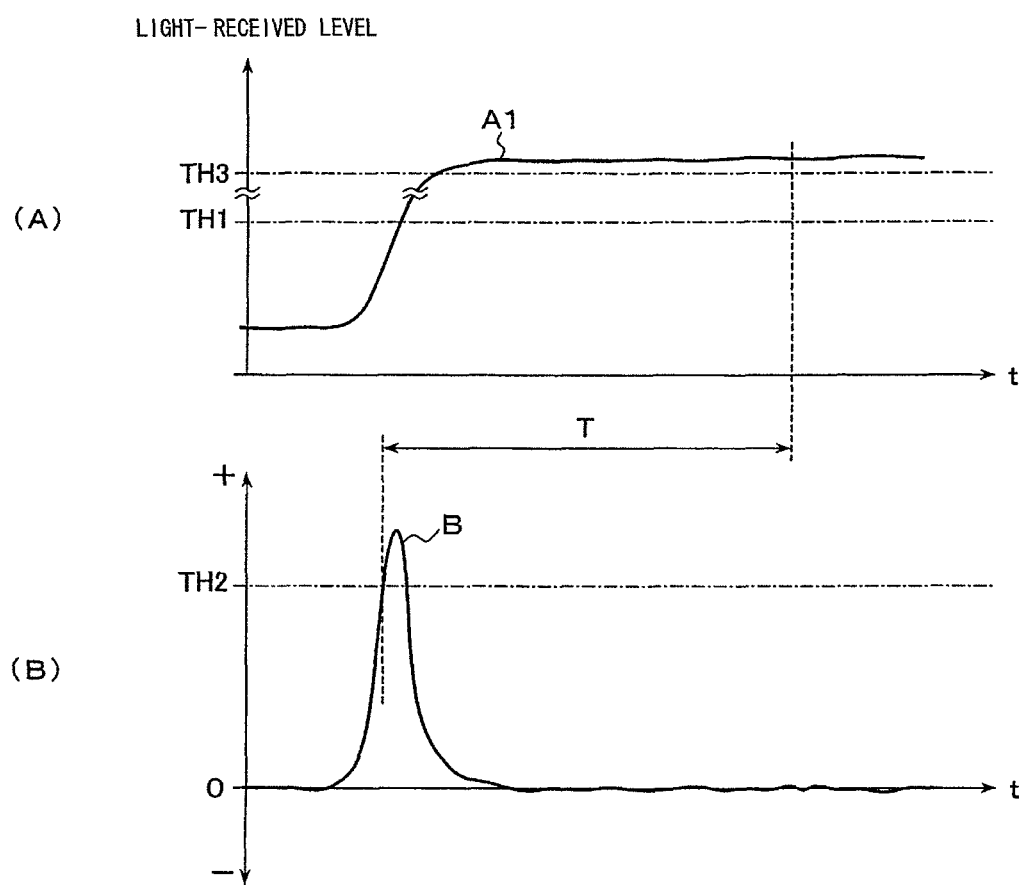
FIG. 29 is a time chart obtained when a foreign substance adheres to the outer surface of the sensor body near the smoke-sensing point P.

FIG. 29 shows a case where a relatively large foreign substance such as a large insect adheres to and sticks to the outer surface 118 of the sensor body near the smoke-sensing point P in the outside open space. The light-received data A1 changes so as to exceed the obstacle threshold TH3, and remains at the level. Accordingly, the differential value B changes significantly to a positive direction so as to exceed the obstacle threshold TH2 at the rising of the light-received data A1.

A differential value B which is stored immediately before the time the light-received data A exceeds the obstacle threshold TH3 is compared with the false alarm threshold TH2. When the differential value B exceeds the false alarm threshold TH2, it is decided that there is a possibility of an obstacle. In order to check the subsequent changes, the timer is activated when the differential value B exceeds the obstacle threshold TH2, and the sensor stands by until the set time T elapses. Then, the light-received data A1 is checked again after time T elapses. Since the light-received data A exceeds the obstacle threshold TH3 at this time, the obstacle is decided to be continuous, and the output is supplied to indicate the presence of obstacle.

Thus, the smoke sensor according to the third embodiment, in addition to exerting the similar effect as the second embodiment, allows multiple decisions to be made based on the plural pieces of data on the amount of received light, whereby the fire sensing can be even more accurately performed.

Further, since the scattering characteristics are made different by the wavelengths, and the combined effect of the differences in the scattering angles and the wavelengths creates a significant difference in the light intensity of the scattered light depending on the type of the smoke, whereby the types of the smoke can be more accurately distinguished.

Further, since the plural light-emitting elements are arranged at solid-angle, the smoke-sensing point, which is a crossing point of the light axis of the light-emitting element and the light axis of the light-receiving element, can be set in a space outside the outer surface of the sensor body for the sensing of the light scattered by the smoke.

Further, since the amount of received scattered light generated from the light from the first light-emitter and the amount of received scattered light generated from the light from the second light-emitter are compared, it is possible to find the ratio of the two and compare the obtained ratio with the threshold. Thus, the type of the smoke can be identified so as to allow for more accurate fire sensing.

Further, since the light-receiving element is set to have the angle of field of view of 5 degrees or less, the size of the area for the sensing of scattered light in the smoke-sensing space can be set to a requisite minimum, whereby the influence by the outside light can be prevented.

Further, since the light-emitting element emits collimated parallel beam, the size of the area for the sensing of scattered light in the smoke-sensing space can be set to a requisite minimum, whereby the influence by the outside light can be prevented.

Next, a fourth embodiment will be described. Though the fourth embodiment is configured basically similarly to the third embodiment, the fourth embodiment is different from the third embodiment in that the scattering angle and the direction of polarization of the two light-emitting elements are different from those in the third embodiment. The configuration and the method of the fourth embodiment is, if not particularly specified otherwise, similar to those of the third embodiment, and the components with the same functions are referred to by the same name or denoted by the same reference characters as the third embodiment.

FIG. 30 schematically describes the configuration of a smoke-sensing unit of the fourth embodiment. In FIG. 30, a first light-emitting element 125, a second light-emitting element 129, and a light-receiving element 133 are arranged so as to face the smoke-sensing point P which is the light axis crossing point. The smoke-sensing point P is located in the outside space of the smoke sensor.

The first light-emitting element 125 emits light 128 which has the vertical polarization plane which is vertical to a first scattering plane 127, which is a plane passing through a light axis 125A of the first light-emitting element 125 and a light axis 133a of the light-receiving element 133.

In the present example, the LED is employed as the first light-emitting element 125. Hence, a polarization filter 126 is arranged in front of the first light-emitting element 125, so that emitted light 128 has the vertical polarization plane to the first scattering plane 127. The first scattering angle θ1 formed by the light axis 125a of the first light-emitting element 125 in the first scattering plane 127 and the light axis 133A of the light-receiving element 133 is set, for example, to 70°.

On the other hand, the second light-emitting element 129 emits lights 132 which has a parallel polarization plane to a second scattering plane 131 which is a plane passing through a light axis 129a of the second light-emitting element 129 and the light axis 133A of the light-receiving element 133. Further, the second scattering angle θ2 formed by the light axis 129a of the second light-emitting element 129 and the light axis 133a of the light-receiving element 133 on the second scattering plane 131 is set to a larger angle than the first scattering angle θ1, for example θ2=120°.

Since the LED is employed for the second light-emitting element 129 as well, a polarization filter 130 is arranged in front of the second light-emitting element 129, so that emitted light 132 has the parallel polarization plane.

Since the light 128 emitted from the first light-emitting element 125 has the vertical polarization plane to the first scattering plane 127, and the light 132 emitted from the second light-emitting element 129 has the parallel polarization plane to the second scattering plane 131, the light scattered at the point P and directed to the light-receiving element 133 become light 134 having the parallel polarization plane to the second scattering plane 131 and directed onto the smoke particles.

The three-dimensional arrangement of the configuration of the smoke-sensing unit according to the fourth embodiment, as shown in FIG. 31, includes the first light-emitting element 125, the second light-emitting element 129, and the light-receiving element 133 arranged at solid angles and embedded into the chamber base 114 (not shown) similar to the third embodiment. The smoke-sensing point P which is the light axis crossing point is set in the outside space at the height h of approximately 5 mm from the outer surface 118 of the sensor body.

Specifically, if the positions of the first light-emitting element 125, the second light-emitting element 129, and the light-receiving element 133 are represented as A, B, and C, respectively, as shown in FIG. 31, these points A, B, and C are arranged so that a triangle formed by three points A, B, C, is a base of a trigonal pyramid whose apex is the smoke-sensing point P, i.e., the light axis crossing point, which is located in the outside space of the outer surface of the chamber base 114.

FIG. 32A shows the solid-angle arrangement of the first light-emitting element 125, the second light-emitting element 129, and the light-receiving element 133, with respect to the light axes 25a, 29a, and 33a thereof.

The smoke-sensing point P which is a crossing point of the light axes 125a, 129a, and 133a of the first light-emitting element 125, the second light-emitting element 129, and the light-receiving element 133 is located in the smoke-sensing space outside the outer surface 118 of the sensor body in the chamber base 114 shown in FIGS. 16 to 18. On the other hand, the first light-emitting element 125, the second light-emitting element 129, and the light-receiving element 133 are arranged in the chamber base 114.

FIG. 32B shows the solid-angle arrangement of the point A of the first light-emitting element 125 and the point C of the light-receiving element 133. Here, a plane including the light axes 125a and 133a from the point A of the first light-emitting element 125 and the point C of the light-receiving element 133 is given as the triangle PCA, and an angle formed by the light axis 125a and the light axis 133a on the plane including the triangle PCA is the first scattering angle θ1 of the first light-emitting element 125.

FIG. 32C shows the solid-angle arrangement of the point B of the second light-emitting element 129 and the point C of the light-receiving element 133. Here, the light axes 129a and 133a are present in the plane including the triangle PCB, and a scattering angle formed by the light axis 129a of the second light-emitting element 129 and the light axis 133a of the light-receiving element 133 is given as the second scattering angle θ2 formed by the light axis 129a and the light axis 133a on the plane including the triangle PCB.

FIG. 33 is a list of experimental results of the amount of light-received signal depending on the types of smoke when the scattering angle and the polarization angle are changed in the smoke-sensing unit with the configuration of FIG. 30. In FIG. 33, the scattering angle θ is 70°, 90°, 120°, and the polarization angle φ is set to 0° (horizontal polarization) and 90° (vertical polarization) for each value of the scattering angle θ.

Here in the fourth embodiment, the similar process (FIGS. 26 and 27) is performed by the circuit block (FIG. 19) similar to that in the third embodiment, for the decision on the presence of fire and obstacle. Further, the threshold for deciding whether the smoke is from non-fire, the threshold for deciding whether the fire is the white smoke fire or the black smoke fire can be the same as in the third embodiment.

FIG. 33 shows the amount of light-received signal for each of the case where the light emitted from the first light-emitting element 125 and the second light-emitting element 129 is scattered by the combustion smoke of the filter paper, kerosene, and tobacco. When the amount of the light-received signal of FIG. 33 is examined with respect to the scattering angle θ and the polarization angle φ, the following can be seen.

First, with regards to the variation in the scattering angle θ, the amount of the light-received signal increases as the scattering angle decreases, whereas the amount of the light-received signal decreases as the scattering angle increases, for both the vertically polarized light of the first light-emitting element 125, and the parallel polarized light of the second light-emitting element 129.

On the other hand, when the values are examined for the same scattering angle θ, for example, 70°, the amount of light-received signal for the vertically polarized light of the first light-emitting element 125 is larger than the amount of light-received signal for the parallel polarized light of the second light-emitting element 129.

At the fire judgment, the ratio R of the amount of light-received signal A1 for the light from the first light-emitting element 125 to the amount of light-received signal A2 for the light from the second light-emitting element 129 is calculated as R=A1/A2, and it is decided whether the smoke is of fire or non-fire, and if the smoke is from fire, whether the fire is the white smoke fire or the black smoke fire.

To increase the ratio R, the scattering angle θ1=70°, which is small so as to increase the amount of light-received signal, is selected for the first light-emitting element 125, while the scattering angle θ2=120°, which makes the amount of light-received signal decrease, is selected for the second light-emitting element 129.

On the other hand, when the scattering angle is the same, the amount of light-received signal is larger for the vertically polarized light, and smaller for the parallel polarized light. To obtain a large ratio R, the vertical polarization with the polarization angle φ1=90° is selected for the first light-emitting element 125 to increase the amount of light-received signal, and parallel polarization with the polarization angle θ2=0° is selected for the second light-emitting element 129 to decrease the amount of light-received signal.

Based on the measurement results for the scattering angle θ and polarization angle φ as shown in FIG. 33, in the embodiment of FIG. 31, (1) the first light-emitting element 125 is set so as to have the vertical polarization with the first scattering angle θ1=70°, and (2) the second light-emitting element 129 is set so as to have the parallel polarization with the second scattering angle θ2=120°.

FIG. 34 shows a list of the amount of light-received signal A1 for the light from the first light-emitting element 125 and the amount of light-received signal A2 for the light from the second light-emitting element 129 depending on the types of the combustion material when the polarization direction and the scattering angle are set as (1) and (2) above. Further, the ratio R of the two amounts of light-received signal is calculated and shown.

As is clear from the list of FIG. 34, for the combustion material at the fire, such as the filter paper and kerosene, the ratio R is 4.44, 5.60 and small, whereas for the tobacco which is categorized as non-fire, the ratio R is 16.47 and sufficiently large. Hence, as shown in the flowchart of FIG. 26, decision based on the ratio R and the threshold=10 in step SB9 allows for the secure distinction between the fire and non-fire.

Further, since the smoke generated by the combustion of kerosene of FIG. 34 belongs to the black smoke fire, with the use of the threshold=6 in step SB10 of FIG. 26, it can be decided that it is black smoke fire (combustion fire) in step SB14.

The smoke generated by the fumigation of the cotton lampwick shown in FIG. 23 is not shown in FIG. 34. However, the ratio R thereof is necessarily larger than the value for kerosene. Hence, the ratio R is equal to or larger than the threshold=6 in step SB10 of FIG. 26, the smoke is decided to be from the white smoke fire in step SB10, and when the counter n reaches the count of three, it is decided that the fire occurs.

In the embodiment of FIG. 30, the first scattering angle $\theta 1=70°$ of the first light-emitting element 125 is set as an example. Practically, $\theta 1$ is set to a value equal to or lower than 80°. Further, the second configuration angle $\theta 2$ of the second light-emitting element 129 is set to 120° as an example. Practically, $\theta 2$ may be set to a value equal to or higher than 100°.

Thus, in addition to exerting the same effect as the third embodiment, the fourth embodiment has the following effect. The scattering characteristic is made different by the polarization direction of the light, and at the same time the scattering angles of the light-receiving elements in two light-emitting units are made different. Thus, the scattering characteristic is made different for each type of smoke, and accuracy in smoke identification can be improved.

A fifth embodiment will be described. When the smoke-sensing point is set outside the light scattering type smoke sensor, the smoke does not stay inside the smoke chamber as in the conventional smoke sensor, whereby the concentration of the smoke can be more accurately reflected in the fire sensing. The fifth embodiment is characterized in that the processing is performed for more accurate sensing of fire with the use of such characteristic. The configuration and the method of the fifth embodiment are, if not specifically described otherwise, similar to those of the first embodiment, and the components with the same functions are referred to by the same name, or denoted by the same reference characters as in the first embodiment.

In the fifth embodiment, the light scattering type smoke sensor is configured as shown in FIG. 1, and the basic electric configuration thereof is as shown in FIG. 5. In the fifth embodiment, a first fire threshold TH1 and a second fire threshold TH2 are set as the thresholds for fire sensing. The first fire threshold TH1 and the second fire threshold TH2 are stored in the storing unit 17 in advance by an optional manner. The first fire threshold TH1 serves to indicate that the smoke concentration in the monitoring area reaches a level which is higher than a normal time (clean air time) and indicates possibility of fire occurrence though not high enough to allow for determination of fire occurrence. The second fire threshold TH2 is set to a higher level than the first fire threshold TH1 (second fire threshold TH2>first fire threshold TH1), and indicates that the smoke concentration in the monitoring area is higher than the normal time (clean air time) and allows for determination of fire occurrence.

In the fifth embodiment, the elapse of time since the fire sensing level exceeds the first fire threshold TH1 is judged based on a first set time TA1 as a standard for judgment, whereas the elapse of time since the fire sensing level exceeds the second fire threshold TH2 is judged based on a second set time TA2 as a standard for judgment. The first set time TA1 and the second set time TA2 are stored in the storing unit 17 by an optional manner in advance.

Next, a fire decision process in the fifth embodiment will be described. FIG. 35 is a flowchart of the fire judgment process. First in step SD1, it is checked whether the amount of received light A is lower than the first fire threshold TH1 or not. When the amount of received light A exceeds the first fire threshold TH1, the process proceeds to step SD2, where the counting of the first set time TA1 starts. After the counting starts, the elapse of the first set time TA1 is checked in step SD3. Meanwhile, whether the amount of received light A remains at a level equal to or higher than the first fire threshold TH1 or not is continuously monitored in step SD4. When the amount of received light A becomes lower than the first fire threshold TH1 before the first set time TA1 elapses, it is decided that the smoke concentration rises merely temporarily due to causes other than fire. In this case, no particular output is given to indicate fire decision.

On the other hand, when the amount of received light A remains to be at a level equal to or higher than the first fire threshold TH1 until the first set time TA1 elapses, the process proceeds to step SD5, where the elapse of the second set time TA2 is monitored. Meanwhile, it is continuously monitored whether the amount of received light A becomes equal to or higher than the fire threshold TH2 or not. When the amount of received light A becomes lower than the fire threshold TH2 before the second set time TA2 elapses, it is decided that the smoke concentration rises merely temporarily due to causes other than fire. In this case, no particular output is given to indicate fire decision. On the other hand, when the amount of received light A remains to be equal to or higher than the second fire threshold TH2 after the second set time TA2 elapses, it is decided that the fire occurs, and output is given to indicate fire decision in step SD7.

A background, an effect, or the like for the above described processing will be described. The conventional light scattering type smoke sensor detects fire by introducing the smoke inside the smoke chamber. Hence, it takes time until the smoke flows into the smoke chamber, which may cause delay in fire sensing. Further, once the smoke enters the smoke chamber, it takes time until the smoke flows out from the smoke chamber. Then, even when the smoke concentration outside the smoke chamber is already low, the smoke concentration inside the smoke chamber remains high, which can induce false alarm.

For example, in the conventional light scattering type smoke sensor provided with the smoke chamber, the changes in the smoke concentration of the smoke of the fire tends to resemble to the changes in the smoke concentration of the smoke generated by causes other than fire (e.g., tobacco or cooking). In other words, though the smoke concentration of the smoke of the fire tends to keep rising by nature, the smoke concentration of the smoke by tobacco, cooking, or the like tends to fluctuate. Particularly, when the smoke concentration becomes low, the level becomes extremely lower than the level of the smoke concentration of the smoke of the fire. Such difference in variations in smoke concentration is detected merely as a minor difference in the conventional light scattering type smoke sensor provided with the smoke chamber.

Figure 36:
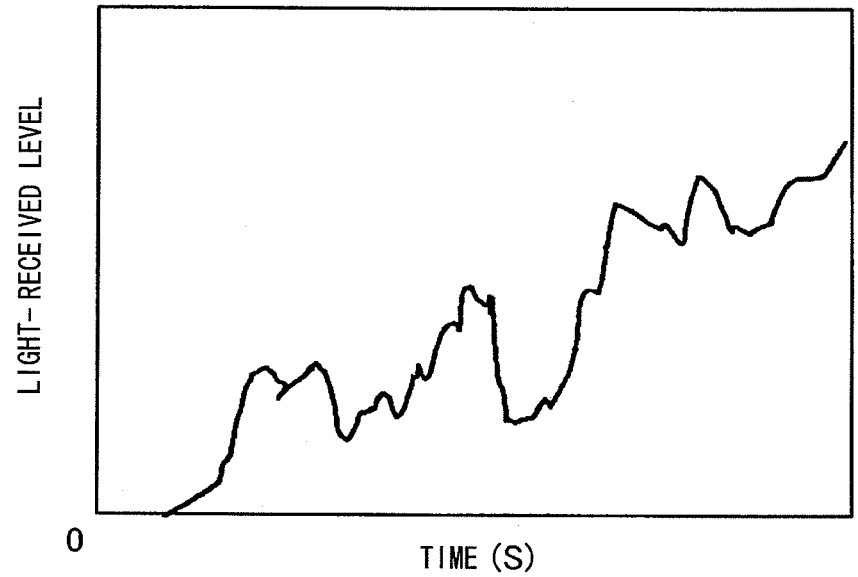
FIG. 36 is a graph of relation between light-received level against time for smoke of tobacco in the conventional light scattering type smoke sensor and including a smoke chamber.
Figure 37:
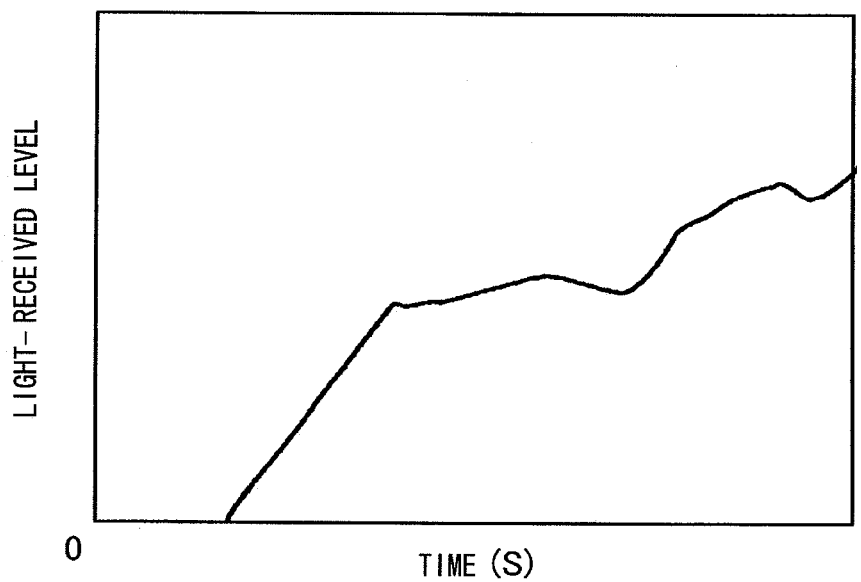
FIG. 37 is a graph of relation between light-received level against time for smoke of fire in the conventional light scattering type smoke sensor and including the smoke chamber.
Figure 38:
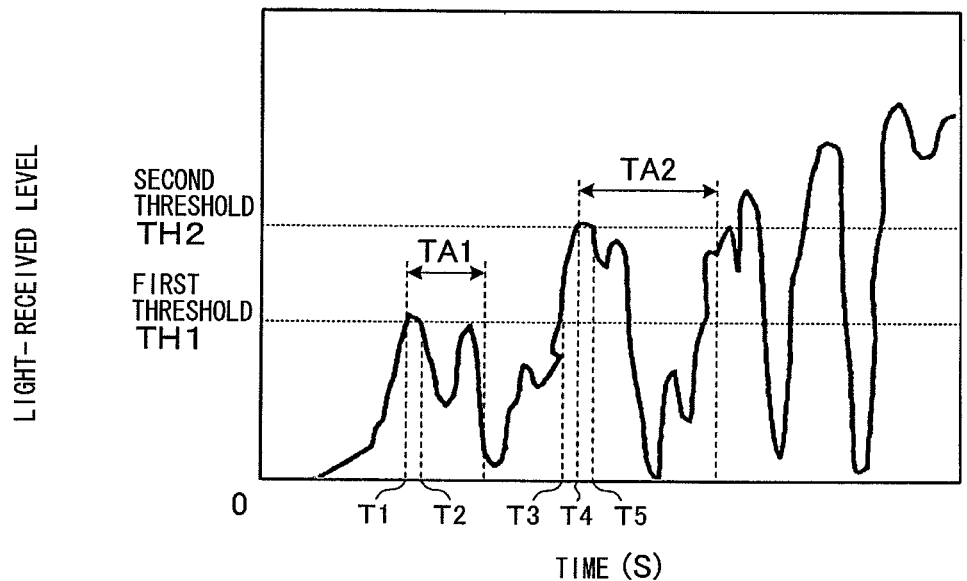
FIG. 38 is a graph of relation between light-received level against time for smoke of tobacco in the light scattering type smoke sensor according to the fifth embodiment.
Figure 39:
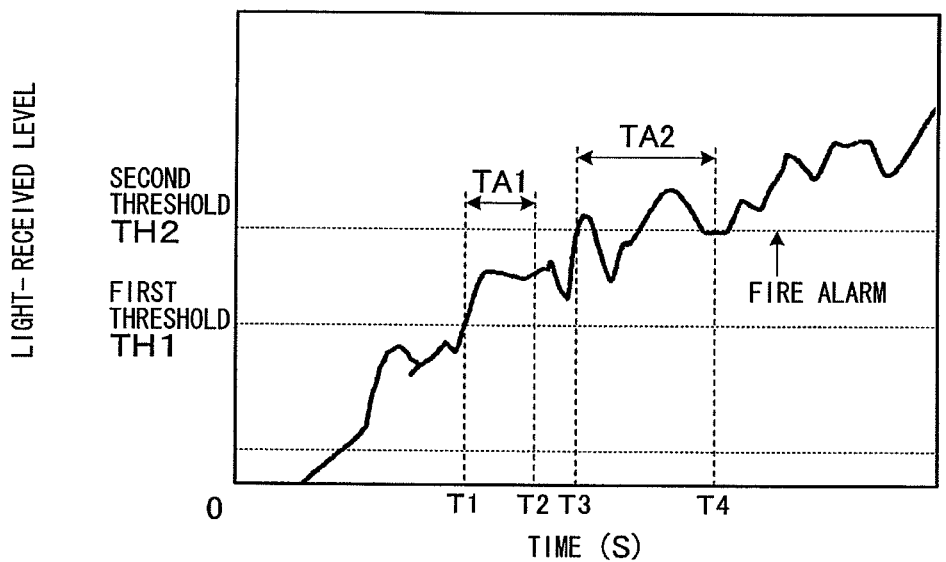
FIG. 39 is a graph of relation between light-received level against time for smoke of fire in the light scattering type smoke sensor according to the fifth embodiment.

FIG. 36 shows a relation between light-received level and time with respect to the smoke of tobacco in the conventional light scattering type smoke sensor provided with the smoke chamber. FIG. 37 shows a relation between the light-received level and time with respect to the smoke of the fire in the conventional light scattering type smoke sensor provided with the smoke chamber. Further, FIG. 38 shows a relation between the light-received level and time with respect to the smoke of tobacco in the light scattering type smoke sensor of the fifth embodiment. FIG. 39 shows a relation between the light-received level and time with respect to the smoke of the fire in the light scattering type smoke sensor of the fifth embodiment. In FIGS. 36 to 39, the horizontal axis represents time, and the vertical axis represents light-received level.

First, when the light-received level for the smoke of tobacco shown in FIG. 36 is compared with the light-received level for the smoke of fire shown in FIG. 37, it can be seen that though the fluctuation is slightly larger in the light-received level for the smoke of tobacco, the graphs show generally similar transitions. Such similarity comes from the fact that since the inflow and outflow of the smoke to/from the smoke chamber take time, the smoke tends to stay inside the smoke chamber and the light-received level is equalized. Hence, mutual differentiation of the smoke of tobacco and the smoke of fire is difficult to achieve based on such light-received level.

On the other hand, when the light-received level for the smoke of tobacco shown in FIG. 38 is compared with the light-received level for the smoke of fire shown in FIG. 39, the fluctuation is larger in the light-received level for the smoke of tobacco, which marks notable difference from the light-received level for the smoke of fire. In the fifth embodiment, the fire is distinguished from the non-fire through the processing as shown in FIG. 35 focusing such point.

According to the process shown in FIG. 35, even when the light-received level exceeds the first threshold TH1 due to the generation of smoke of tobacco (time T1 of FIG. 38), if the light-received level becomes lower than the first threshold TH1 (time T2 of FIG. 38) before the first set time TA1 elapses, the sensor does not decide that the fire occurs. Further, even when the light-received level exceeds the first threshold TH1 (time T3 of FIG. 38) and further exceeds the second threshold TH2 (time T4 of FIG. 38), if the light-received level becomes lower than the second threshold TH2 before the second set time TA2 elapses (time T5 of FIG. 38), the sensor does not decide that the fire occurs. In brief, even if the light-received level becomes high, if such state does not continue for a predetermined time period, the sensor decides that the smoke is caused by non-fire, and does not raise fire alarm, whereby false alarm can be prevented.

On the other hand, when the smoke is generated from the fire, and the light-received level exceeds the first threshold TH1 (time T1 of FIG. 39) and remains higher than the first threshold TH1 even after the first set time TA1 elapses (time T2 of FIG. 39), and further, if the light-received level exceeds the second threshold TH2 (time T3 of FIG. 39) and such state continues even after the second set time TA2 elapses (time T4 of FIG. 39), the sensor raises fire alarm.

Specifically, the first threshold TH1, the second threshold TH2, the first set time TA1, and the second set time TA2 can take any values, and may be determined based on the results of experiments or the like. For example, the first set time TA1 may be set to 30 seconds, and the second set time TA2 may be set to 60 seconds.

Thus, in addition to the same effect obtained in the first embodiment, the fifth embodiment utilizes the feature that the different tendencies in behaviors of the smoke of fire and non-fire can be directly reflected in the sensing result, thereby exerting an effect that the smoke from fire and non-fire can be distinguished from each other, and allows for the prevention of the false alarm.

Hereinabove, the first to the fifth embodiments are described. Advantages and variations other than those described above may be readily deduced by those skilled in the art. Hence, the present invention in its broad sense is not limited to the details and the representative embodiments shown herein. In other words, various modifications can be made within the concept and the scope of the present invention as defined by the appended claims and their equivalents.

For example, features of the first to the fifth embodiments may be mutually adoptable. For example, the processing with the first and the second fire threshold TH1 and TH2 as in the fifth embodiment may be incorporated into the light scattering type smoke sensor provided with plural light emitters as in the third embodiment.

Further, on the surface of the outer surface 7 of the sensor body of the first embodiment, an uneven screen may be attached to prevent the adherence of insects or foreign substances in a way that the screen does not protrude by a notable amount compared with other parts. In the first embodiment, the transparent cover 9 is attached so as to cover the entire outer surface 7 of the sensor body. The protective cover 9, however, may be arranged only on the light-emitting opening 5*b* and the light-receiving opening 6*b*. Further, since the outer surface 7 of the sensor body faces downwards when the smoke sensor is installed on the ceiling, the smoke sensor may be configured as an open-type sensor in which the transparent cover 9 is not attached to the light-emitting opening 5*b* and the light-receiving opening 6*b*.

In the fourth embodiment of FIG. 30, the LED is employed as the first light-emitting element 125 and the second light-emitting element 129, and combined with the polarization filters 126 and 130, respectively, so that the first light-emitting element 125 emits light 128 with vertical polarization plane and the second light-emitting element 129 emits light 132 with parallel polarization plane. The polarization filters 126 and 130 may become unnecessary, however, if a laser diode emitting polarized light is employed as the first light-emitting element 125 and the second light-emitting element 129 instead.

In the fourth embodiment, the wavelengths of the first light-emitting element 125 and the second light-emitting element 129 are made equal. However, the accuracy in smoke identification may be further enhanced when the wavelengths are made different.

As shown in FIGS. 16 to 21, the wavelengths and the scattering angles of two light-emitting elements are made different in the smoke-sensing unit. As an alternative embodiment, two light-receiving elements may be provided for two light-emitting elements 109 and 110 as far as the relation of the wavelengths and the scattering angles of the first light-emitting element 109 and the second light-emitting element 110 are maintained.

Still alternatively, a light-emitting element with wider emission spectrum, such as incandescent lamp or white LED may be employed as the light-emitting element, so that only one light-emitting element is sufficient. Then, the optical paths are arranged by provision of a wavelength-switching filter to the light-emitting element, so that the light is emitted from positions corresponding to the first light-emitting element 109 and the second light-emitting element 110 shown in FIG. 16.

The smoke-sensing unit is configured so that the two light-emitting elements 125 and 129 have different scattering angles and polarization directions in FIG. 30. Alternatively, two separate light-receiving elements may be provided at different positions respectively for the two light-emitting elements 125 and 129 with different polarization planes.

The polarization planes of light emitted from two light-emitting elements 125 and 129 may be adjusted as appropriate to optimize the detecting state. For the adjustment, the polarization filters 126 and 130 of FIG. 30 may be mechanically rotated, or the polarization planes 128 and 132 may be changed through the driving of a known liquid crystal filter, so that the polarization direction of the polarization plane 134 is properly adjusted.

Industrial Applicability

As can be seen from the foregoing, the light scattering type smoke sensor according to the present invention is useful for sensing smoke to notify the occurrence of fire, and particularly suitable for building a smoke sensing system with a good appearance by reducing the amount of protrusion of the light scattering type smoke sensor from the installed surface such as a ceiling surface, and for giving an accurate notification of fire by distinguishing different types of smoke from each other.

The invention claimed is:

1. A light scattering type smoke sensor comprising:
   a sensor body;
   a light-emitter that is incorporated in the sensor body to emit light toward an open smoke-sensing space located outside the sensor body;
   a light-receiver that is incorporated in the sensor body to receive scattered light generated by the light emitted from the light-emitter to the smoke-sensing space, and to output a light-received signal corresponding to an amount of received light scattered; and
   a fire judging unit that judges presence/absence of fire occurrence based on the amount of received light identified by the light-received signal output from the light-receiver, wherein
   the fire judging unit judges that fire occurs, when the amount of received light exceeds a predetermined first fire threshold for a time equal to or longer than a predetermined first set time, and the amount of received light exceeds a predetermined second fire threshold which is higher than the first fire threshold for a time equal to or longer than a predetermined second set time.

2. The light scattering type smoke sensor according to claim 1, wherein the fire judging unit judges the present/absence of the fire occurrence based on the amount of received light and a differential value of the amount of received light.

3. The light scattering type smoke sensor according to claim 2, wherein the fire judging unit judges that fire occurs when the amount of received light exceeds a predetermined fire threshold and the differential value of the amount of received light is equal to or lower than a predetermined false alarm threshold.

4. The light scattering type smoke sensor according to claim 3, wherein
   when the amount of received light exceeds the predetermined fire threshold, and the differential value of the amount of received light exceeds the predetermined false alarm threshold, the fire judging unit checks whether the amount of received light exceeds a predetermined obstacle threshold or not when a predetermined time elapses since the time the differential value exceeds the predetermined false alarm threshold, and judges that there is an obstacle for fire sensing when the amount of received light exceeds the obstacle threshold.

5. The light scattering type smoke sensor according to claim 1, wherein the light-emitter has plural light-emitters.

6. The light scattering type smoke sensor according to claim 5, wherein
   the light-emitter comprises a first light-emitter that emits light of a first wavelength, and second light-emitter that emits light of a second wavelength which is shorter than the first wavelength; and
   a first scattering angle formed by mutual crossing of a light axis of the first light-emitter and a light axis of the light-receiving element is smaller than a second scattering angle formed by mutual crossing of a light axis of the second light-emitter and the light axis of the light-receiving element.

7. The light scattering type smoke sensor according to claim 5, wherein:
   a central wavelength of the first wavelength is equal to or longer than 800 nm;
   a central wavelength of the second wavelength is equal to or shorter than 500 nm;
   the first scattering angle falls within a range of approximately 20° to 50°; and
   the second scattering angle falls within a range of approximately 100° to 150 °.

8. The light scattering type smoke sensor according to claim 5, wherein
   the light-emitter comprises a first light-emitter and a second light-emitter;
   the first light-emitter emits light having a polarization plane vertical to a first scattering plane that passes through a light axis of the first light-emitter and a light axis of the light-receiving element;
   the second light-emitter emits light having a polarization plane parallel to a second scattering plane that passes through a light axis of the second light-emitter and the light axis of the light-receiving element; and
   a first scattering angle formed by mutual crossing of the light axis of the first light- emitter and the light axis of the light-receiving element is smaller than a second scattering angle formed by mutual crossing of the light axis of the second light-emitter and the light axis of the light-receiving element.

9. The light scattering type smoke sensor according to claim 8, wherein:
   the first scattering angle is equal to or smaller than 80°; and
   the second scattering angle is equal to or larger than 100°.

10. The light scattering type smoke sensor according to claim 5, wherein the plural light-emitters are arranged at solid angles, so that planes including respective light axes of the plural light-emitters and the light axis of the light-receiving element are substantially not identical with each other.

11. The light scattering type smoke sensor according to claim 5, wherein:
    the light-emitter includes a first light-emitter and a second light-emitter; and
    the fire judging unit compares an amount of received light by the light-receiver with respect to scattered light generated from the light emitted by the first light-emitter and scattered by smoke with an amount of received light by the light-receiver with respect to scattered light generated from the light emitted by the second light-emitter and scattered by the smoke, identifies a type of the smoke based on the comparison result, and judges the presence/absence of fire occurrence based on a standard corresponding to the type of the smoke.

12. The light scattering type smoke sensor according to claim 1, wherein a mutual crossing point of the light axis of the light-emitter and the light axis of the light-receiver in the smoke-sensing space is at least approximately 5 mm away from the sensor body.

13. The light scattering type smoke sensor according to claim 1, wherein at least one portion of an outer surface of the sensor body is configured by an insect avoiding material, or an insect avoiding agent is applied or made to permeate to at least one portion of the outer surface of the sensor body.

14. The light scattering type smoke sensor according to claim 1, wherein the light-receiver has an angle of field of view not larger than 5 degrees.

15. The light scattering type smoke sensor according to claim 1, wherein the light-emitter emits collimated parallel beam.

16. The light scattering type smoke sensor according to claim 1, further comprising a logarithmic amplifier which amplifies the light-received signal output from the light-receiver.

17. The light scattering type smoke sensor according to claim 1, further comprising:

a light emission controller that drives the light-emitter to intermittently emit light by using a modulated light-emission signal; and an amplifier that amplifies the light-received signal output from the light-receiver in synchronization with the modulated light-emission signal.

18. The light scattering type smoke sensor according to claim 17, further comprising a light emission controller that drives the light-emitter to intermittently emit light by using a modulated light-emission signal, wherein:

the light-emitter emits light within a visible light wavelength band; and the light emission controller drives to intermittently emit light at a light-emission pulse width of equal to or smaller than 1 millisecond.

19. The light scattering type smoke sensor according to claim 18, wherein the light emission controller sets a total light emission time period in an intermittent light emission equal to or smaller than 1 millisecond.

* * * * *